(12) United States Patent
Braun et al.

(10) Patent No.: US 7,569,582 B2
(45) Date of Patent: Aug. 4, 2009

(54) AMINOTROPANE DERIVATIVES, PREPARATION THEREOF AND THERAPEUTIC USE THEREOF

(75) Inventors: Alain Braun, Boulogne Billancourt (FR); Bruno Cornet, Perthes-en-Gatinais (FR); Gilles Courtemanche, Lacroix-Falgarde (FR); Olivier Crespin, Cergy (FR); Cecile Pascal, Rueil Malmaison (FR)

(73) Assignee: Sanofi-Aventis, Paris (FR)

( * ) Notice: Subject to any disclaimer, the term of this patent is extended or adjusted under 35 U.S.C. 154(b) by 218 days.

(21) Appl. No.: 11/626,973

(22) Filed: Jan. 25, 2007

(65) Prior Publication Data

US 2007/0191361 A1 Aug. 16, 2007

Related U.S. Application Data

(63) Continuation of application No. PCT/FR2005/001856, filed on Jul. 20, 2005.

(30) Foreign Application Priority Data

Jul. 29, 2004 (FR) .................................. 04 08372

(51) Int. Cl.
*A01N 43/42* (2006.01)
*C07D 451/00* (2006.01)

(52) U.S. Cl. ........................ 514/304; 546/129; 546/132

(58) Field of Classification Search ................. 546/129, 546/132; 514/304
See application file for complete search history.

(56) References Cited

U.S. PATENT DOCUMENTS 5,968,929 A * 10/1999 Blythin et al. ............... 514/215

FOREIGN PATENT DOCUMENTS

| WO | WO 02/059095 | 8/2002 |
|---|---|---|
| WO | WO 03/061660 | 7/2003 |

OTHER PUBLICATIONS

Haqq et al., The Journal of clinical endocrinology and metabolism, (Jan. 2003) vol. 88, No. 1, pp. 174-178.*
Holder, J.R., et. al., Melanocortin Ligands: 30 Years of Structure-Activity Relationship (SAR) Studies, Medicinal Research Reviews vol. 24, No. 3, pp. 325-356 (2004).
Irani, B.G., et. al., Progress in the Development of Melanocorting Receptor Selective Ligands, Current Pharmaceutical Design vol. 10, No. 28 (2004) pp. 3443-3479 (37).

* cited by examiner

*Primary Examiner*—D. Margaret Seaman
*Assistant Examiner*—Niloofar Rahmani
(74) *Attorney, Agent, or Firm*—Balaram Gupta

(57) ABSTRACT

The present invention relates to compounds of formula (I) as defined herein that are melanocortin receptor agonists, to the preparation thereof and to the therapeutic use thereof in the treatment and in the prevention of obesity, diabetes and sexual dysfunctions that can affect both sexes, in the treatment of cardiovascular diseases, and also in anti-inflammatory uses or in the treatment of alcohol dependency.

15 Claims, No Drawings

AMINOTROPANE DERIVATIVES, PREPARATION THEREOF AND THERAPEUTIC USE THEREOF

BACKGROUND OF THE INVENTION

The present invention relates to compounds that are melanocortin receptor agonists, to the preparation thereof and to the therapeutic use thereof.

Melanocortin receptors (MC-Rs) belong to the superfamily of G protein-coupled seven-transmembrane domain receptors. Their transduction pathway involves the production of cAMP (Cone, R. D., *Recent Prog. Horm. Res.*, 1996, 51, 287). Five MC—R subtypes have currently been described, MC1-R, MC2-R, MC3-R, MC4-R and MC5-R, and are expressed in various tissues, such as the brain (MC3, 4, 5-R), the exocrine glands (MC5-R), the adrenals (MC2-R) and the skin (MC1-R), as regards the main ones. The natural ligands of MC-Rs are, as regards the agonists, ACTH, and α-, β- and γ-MSH, and as regards the antagonists, agouti protein and agouti-related protein. None of the natural ligands is very selective for one of the subtypes, with the exception of γ-MSH, which have a certain selectivity for MC3-R.

The melanocortin system is involved in many physiological processes, including pigmentation, inflammation, eating behaviour and sexual behaviour (in particular erectile function), energetic balance (regulation of body weight and lipid storage), exocrine functions, neuronal protection and regeneration, immunomodulation, analgesia, etc.

In particular, it has been demonstrated that MC4-R is involved in sexual behaviour (Van der Ploeg, L. H., *Proc. Natl. Acad. Sci. USA*, 2002, 99, 11381; Martin, W. J., *Eur. J. Pharmacol.*, 2002, 454, 71). It has also been demonstrated, by means of mouse models specifically devoid of certain MC-Rs (knockout mice), that the central MC-Rs (MC3 and 4-R) are involved in eating behaviour, obesity, the metabolism and energetic balance (Huszar, D., *Cell*, 1997, 88(1), 131; Chen, A. S., *Nat. Genet.*, 2000, 26(1), 97; Butler, A. A., *Trends Genet.*, 2001, 17, pp. 50-54). Thus, MC4-R knockout mice are hyperphagic and obese. In parallel, MC3 and/or 4R antagonists promote food intake, whereas the stimulation of MC4-Rs by an endogenous agonist, such as α-MSH, produces a satiety signal.

These observations imply that the stimulation of central MC3-R and/or MC4-R, reducing food intake and body weight, is a promising approach for treating obesity, which is an aggravating risk for many other pathologies (hypertension, diabetes, etc.). Thus, research studies have made it possible to identify, initially, peptides, pseudopeptides or cyclic peptides capable of interacting with MC-Rs and of thus modulating food intake.

In order to maintain an effective weight loss in the long term and thus to limit comorbidities, a long-term daily treatment must be envisaged. This implies that a medicament, for this therapeutic indication, must be able to be administered simply by the patient. Oral administration must therefore be favoured. Now, peptide compounds are not generally the most suitable for satisfying this need. For this reason, it is important to develop small non-peptide molecules.

In this perspective, international PCT applications published under the numbers WO 02/059095, WO 02/059108, WO 03/009850 and WO 03/061660 describe piperazine-type derivatives. Other applications describe piperidine-type derivatives, such as WO 03/092690 and WO 03/093234. Applications WO 99/64002 and WO 01/70337 describe spiropiperidine-type derivatives. Application WO 01/91752 describes derivatives containing a piperidine unit fused with a pyrazolyl ring. Application WO 02/059107 describes piperidine-type and piperazine-type derivatives substituted with a bicyclic structure. Applications WO 02/059117, WO 02/068388 and WO 03/009847 describe piperidine-type and/or piperazine-type derivatives substituted with a phenyl ring. As regards application WO 03/094918, it describes piperazine-type derivatives substituted with a phenyl or pyridinyl ring. Mention may also be made of applications WO 00/74679, WO 01/70708, WO 02/15909, WO 02/079146, WO 03/007949 and WO 04/024720, which describe substituted piperidine-type derivatives, or else application WO 04/037797; the compounds described in those patent applications always contain an amide function, that mimics the peptide structures previously known.

Faced with the constant need to improve existing therapies for the pathologies mentioned above, the inventors gave themselves the aim of providing novel compounds that are melanocortin receptor agonists.

SUMMARY OF THE INVENTION

A subject of the present invention is compounds corresponding to formula (I)

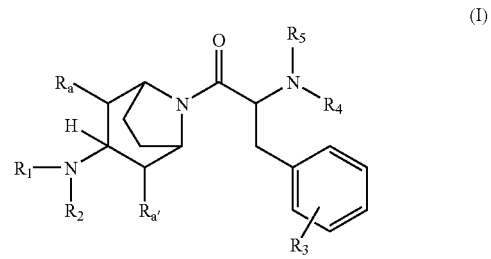

in which:

$R_a$ and $R_{a'}$, which may be identical to or different from one another, represent a hydrogen atom, or an alkyl or cycloalkyl group, $R_1$ represents a hydrogen atom, or an alkyl, cycloalkyl, heterocycloalkyl or aryl group, $R_2$ represents a group of formula —$(CH_2)_x$—$(CO)_y$—Y or —$(CO)_y$—$(CH_2)_x$—Y, in which:

x=0, 1, 2, 3 or 4, y=0 or 1,

Y represents a hydrogen atom, or a hydroxyl, alkyl, cycloalkyl, alkoxy, aryl, heteroaryl or —$NR_{11}R_{12}$ group, Y being different to a hydrogen atom when x=y=0, $R_{11}$ and $R_{12}$ which may be identical to or different from one another, represent a hydrogen atom, or an alkyl, cycloalkyl, alkoxy or —$NR_{13}R_{14}$, or else $R_{11}$ and $R_{12}$ form, together with the nitrogen atom to which they are attached, a mono- or bicyclic structure containing from 4 to 10 ring members and optionally comprising 1 to 3 additional hetero atoms and/or 1 to 3 ethylenic or acetylenic unsaturations, this ring being optionally substituted in any of the positions with 1 to 3 groups chosen from halogen atoms, and hydroxyl, alkyl, cycloalkyl and alkoxy groups. By way of examples of such cyclic structures, mention may be made of pyrrolidinyl, morpholinyl, pyrrolinyl, isoindolinyl groups, etc., $R_{13}$ and $R_{14}$, which may be identical to or different from one another, represent a hydrogen atom, or an alkyl, cycloalkyl or alkoxy group, or else $R_{13}$ and $R_{14}$ form, together with the nitrogen atom to which they are attached, a mono- or bicyclic structure as defined above, $R_3$ represents 1 to 3 groups, which may be identical to or different from one another, located in any positions of the ring to which they are attached and chosen from halogen atoms, and alkyl, cycloalkyl, —OR, —NRR', —CO—NRR', —NR—CO—R', —NR—CO—NRR', —NR—COOR', —NO$_2$, —CN and —COOR groups, where R and R' are as defined below, $R_5$ represents a hydrogen atom, or an alkyl or cycloalkyl group, $R_4$ is chosen from:

(1) a group of formula (a), (b) or (c) optionally substituted with an oxo group:

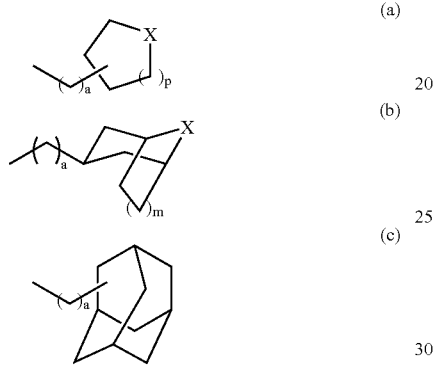

in which each of the rings of formulae (a), (b) and (c) may be substituted, in any positions, with 1 to 4 groups $R_7$, which may be identical to or different from one another, and in which:

a=0, 1, 2 or 3,
p=0, 1, 2 or 3,
m=0, 1 or 2,

X represents an oxygen or sulphur atom, or a ring member —C($R_6$)($R_7$)— or —N($R_{10}$)—, $R_6$ is chosen from:

a hydrogen atom, a halogen atom, a group —(CH$_2$)$_x$—OR$_8$, —(CH$_2$)$_x$—COOR$_8$, —(CH$_2$)$_x$—NR$_8$R$_9$, —(CH$_2$)$_x$—CO—NR$_8$R$_9$ or —(CH$_2$)$_x$—NR$_8$—COR$_9$, in which x=0, 1, 2, 3 or 4, and $R_8$ and $R_9$ are as defined below, an alkyl, cycloalkyl, heterocycloalkyl, aryl, heteroaryl, alkylaryl, alkylheteroaryl, —CO-alkyl, —CO-cycloalkyl, —CO-heterocycloalkyl, —CO-aryl, —CO-heteroaryl, —CO-alkylaryl, —CO-alkylheteroaryl, —CS-alkyl, —CS-cycloalkyl, —CS-heterocycloalkyl, —CS-aryl, —CS-heteroaryl, —CS-alkylaryl, —CS-alkylheteroaryl, —CS—NR$_8$R$_9$ or —C(=NH)—NR$_8$R$_9$ group, a fused or nonfused cycloalkyl or heterocycloalkyl group located in the spiro position on the ring of formula (a) to which it is attached, a cycloalkyl or heterocycloalkyl group fused with an aryl or heteroaryl group, $R_7$ is chosen from hydrogen and halogen atoms, and alkyl, cycloalkyl, aryl, heteroaryl, alkylaryl, alkylheteroaryl, —OR, —O-aryl, —O-heteroaryl, —O-alkylaryl, —O-alkylheteroaryl, —NRR', —CO—NRR', —NR—CO—R', —NR—CO—NRR', —NR—COOR', —NO$_2$, —CN and —COOR groups, where R and R' are as defined below, $R_8$ and $R_9$ are chosen, independently of one another, from a hydrogen atom, and alkyl, cycloalkyl, heterocycloalkyl, aryl, heteroaryl, alkylaryl, alkyl-heteroaryl, —CO-alkyl, —CO-cycloalkyl, —CO-hetero-cycloalkyl, —CO-aryl, —CO-heteroaryl, —CO-alkylaryl, —CO-alkylheteroaryl, —SO$_2$-alkyl, —SO$_2$-cycloalkyl, —SO$_2$-heterocycloalkyl, —SO$_2$-aryl, —SO$_2$-heteroaryl, —SO$_2$-alkylaryl, —SO$_2$-alkylheteroaryl, —C(=NH)—NRR', —COOR, —CO—NRR', —CS—NRR' and —(CH$_2$)$_x$—OR groups, where x=0, 1, 2, 3 or 4, and R and R' are as defined below, the alkyl, cycloalkyl, heterocycloalkyl, aryl and heteroaryl groups being optionally substituted with one or more groups chosen from the groups R, R', —OR, —NRR', —CO—NRR', —NR—CO—R', —NR—CO—NRR', —NO$_2$, —CN and —COOR, OCOR, COR, OCONRR', NRCOOR', or else $R_8$ and $R_9$ together form a cycloalkyl or a heterocycloalkyl;

$R_{10}$ is chosen from:

a hydrogen atom, a group —(CH$_2$)$_x$—OR$_8$, —(CH$_2$)$_x$—COOR$_8$, —(CH$_2$)$_x$—NR$_8$R$_9$, —(CH$_2$)$_x$—CO—NR$_8$R$_9$ or —(CH$_2$)$_x$—NR$_8$—COR$_9$, in which x=0, 1, 2, 3 or 4, and $R_8$ and $R_9$ are as defined above, a cycloalkyl or heterocycloalkyl group fused with an aryl or heteroaryl group, an alkyl, cycloalkyl, heterocycloalkyl, aryl, heteroaryl, alkylaryl, alkylheteroaryl, —CO-alkyl, —CO-cycloalkyl, —CO-heterocycloalkyl, —CO-aryl, —CO-heteroaryl, —CO-alkylaryl, —CO-alkylheteroaryl, —CS-alkyl, —CS-cycloalkyl, —CS-heterocycloalkyl, —CS-aryl, —CS-heteroaryl, —CS-alkylaryl, —CS-alkylheteroaryl, —CS—NR$_8$R$_9$, —C(=NH)—NR$_8$R$_9$, —SO$_2$-alkyl, —SO$_2$-cycloalkyl, —SO$_2$-heterocycloalkyl, —SO$_2$-aryl, —SO$_2$-heteroaryl, —SO$_2$-alkylaryl, —SO$_2$-alkylheteroaryl or —SO$_2$—NR$_8$R$_9$ group, where $R_8$ and $R_9$ are as defined above, or else $R_{10}$ forms, with the nitrogen atom to which it is attached and a carbon atom located in any position of the cyclic structure of formula (a), but not adjacent to said nitrogen atom, a bridge comprising from 3 to 5 members, R and R' represent, independently of one another, a hydrogen atom, or an alkyl, cycloalkyl, heterocycloalkyl, aryl, heteroaryl, alkylaryl or alkylheteroaryl group, or else R and R' can together form a cycloalkyl or a heterocycloalkyl, the alkyl, cycloalkyl, heterocycloalkyl, aryl and heteroaryl groups being optionally substituted with one or more groups chosen from the groups R, R', —OR, —NRR', —CO—NRR', —NR—CO—R', —NR—CO—NRR', —NO$_2$, —CN and —COOR, OCOR, COR, OCONRR', NRCOOR', (2) a group of formula -A-$R_{18}$, -A-CH=N—$R_{19}$, -A-N($R_{20}$)-A'-$R_{19}$, -A-CO—N($R_{20}$)-A'-$R_{19}$, -A-CH(NH$_2$)—$R_{19}$ or -A-N($R_{20}$)—COO-A', in which A and A' represent a linear or branched alkyl group, $R_{18}$ represents a halogen atom, or an —NH$_2$, hydroxyl or phenyl group, $R_{19}$ represents a hydrogen atom, or a hydroxyl, phenyl, benzyl or heteroaryl group, and $R_{20}$ represents a hydrogen atom or a benzyl group, (3) a group of formula (d):

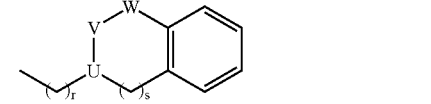

optionally substituted, in any positions, with 1 to 4 groups $R_7$, which may be identical to or different from one another, as defined above, and in which r is equal to 1, 2 or 3, s is equal to 0 or 1, and one of U, V or w represents a nitrogen atom, the others among U, V and W representing methylene ring members (i.e. —CH$_2$— ring members for V and W, and a —CH— ring member for U), or (4) a —(CH$_2$)$_r$-heteroaryl group, where r is equal to 1, 2 or 3.

The compounds of formula (I) contain at least one asymmetric carbon atom. They can therefore exist in the form of enantiomers or of diastereoisomers. These enantiomers and diastereoisomers, and also mixtures thereof, including racemic mixtures, are part of the invention.

DETAILED DESCRIPTION

Among the compounds of formula (I) that are subjects of the invention, preference is given to those in which the carbon atom identified by the asterisk * in the formula below is in an (R) configuration:

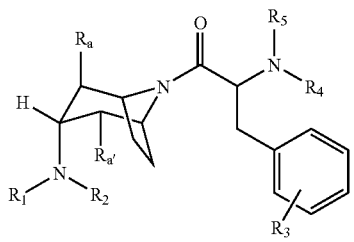

The compounds of formula (I) according to the invention can also exist in the form of mixtures of conformers, which are also part of the invention. They can also exist in the form of cis or trans isomers, or in the form of endo or exo isomers. These isomers, and also the mixture thereof, are part of the invention.

In this regard, the tropane ring of the compounds of formula (I) according to the invention advantageously has an endo configuration, as represented below:

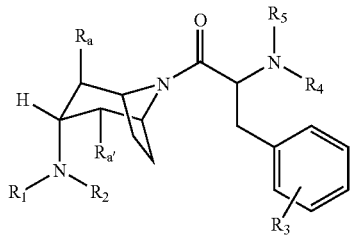

The compounds of formula (I) can exist in the form of bases or of addition salts with acids. Such addition salts are part of the invention.

These salts are advantageously prepared with pharmaceutically acceptable acids, but the salts of other acids that are useful, for example, for purifying or isolating the compounds of formula (I) are also part of the invention.

The compounds of formula (I) can also exist in the form of hydrates or of solvates, i.e. in the form of associations or of combinations with one or more molecules of water or with a solvent. Such hydrates and solvates are also part of the invention.

In the context of the present invention, and unless otherwise mentioned in the text, the term:

"a halogen atom" is intended to mean: a fluorine, a chlorine, a bromine or an iodine;

"an alkyl group" is intended to mean: a saturated or unsaturated (i.e. comprising between 1 and 3 unsaturations of ethylenic or acetylenic type), linear, cyclic or branched aliphatic group comprising from 1 to 6 carbon atoms. By way of examples, mention may be made of methyl, ethyl, propyl, isopropyl, butyl, isobutyl, tert-butyl, pentyl, neopentyl groups, etc., and the cycloalkyl groups defined below, and also alkyl groups only partially cyclized, such as the methyl-cyclopropyl group. Such an alkyl group may be substituted with 1 or more groups (for example with 1 to 6 groups) chosen from halogen atoms (resulting, for example, in a —CF$_3$ group) and the groups R, R', —OR, —NRR', —CO—NRR', —NR—CO—R', —NR—CO—NRR', —NO$_2$, —CN and —COOR, OCOR, COR, OCONRR', NRCOOR'; where R and R' represent, independently of one another, a hydrogen atom, or an alkyl, cycloalkyl, heterocycloalkyl, aryl, heteroaryl, alkylaryl or alkylheteroaryl group, or can together form a cycloalkyl or a heterocycloalkyl;

"a cycloalkyl group" is intended to mean: a cyclic alkyl group comprising between 3 and 8 carbon atoms, all the carbon atoms being involved in the cyclic structure. By way of examples, mention may be made of cyclopropyl, cyclobutyl, cyclopentyl, cyclohexyl groups, etc. Such a cycloalkyl group may be substituted as described above for the alkyl group;

"a heterocycloalkyl group" is intended to mean: a cycloalkyl group as defined above, also comprising between 1 and 4 hetero atoms, such as nitrogen, oxygen and/or sulphur. Such a heterocycloalkyl group may be substituted as described above for the cycloalkyl group and may comprise one or more, for example 1 or 2, ethylenic or acetylenic unsaturations. By way of examples of heterocycloalkyl groups, mention may be made of piperidinyl and tetrahydropyan groups;

"an alkoxy group" is intended to mean: an —O-alkyl radical, where the alkyl group is as defined above;

"an aryl group" is intended to mean: a cyclic aromatic group comprising between 5 and 10 ring members, for example a phenyl group. Such an aryl group may be substituted with 1 or more groups (for example with 1 to 6 groups) chosen from halogen atoms (resulting, for example, in a —CF$_3$ group), and alkyl R, R', —OR, —NRR', —CO—NRR', —NR—CO—R', —NR—CO—NRR', —NO$_2$, —CN, COR and —COOR groups, where R and R' represent, independently of one another, a hydrogen atom, or an alkyl, cycloalkyl, heterocycloalkyl, aryl, heteroaryl, alkylaryl or alkylheteroaryl group, or can together form a cycloalkyl or heterocycloalkyl;

"an alkylaryl group" is intended to mean: an alkyl group as defined above, itself substituted with an aryl group as defined above. Such an alkylaryl group is, for example, a benzyl group;

"a heteroaryl group" is intended to mean: a cyclic aromatic group comprising between 5 and 10 ring members and comprising between 1 and 6 hetero atoms, such as nitrogen, oxygen and/or sulphur. By way of example, mention may be made of the pyridinyl group and the fyryl group. Such a heteroaryl group may be substituted as described above for the aryl group;

"an alkylheteroaryl group" is intended to mean: an alkyl group as defined above, itself substituted with a heteroaryl group as defined above.

Among the compounds of formula (I) that are subjects of the invention, mention may be made of those in which $R_a$, $R_{a'}$, $R_2$, $R_3$, $R_4$ and $R_5$ are as defined above and $R_1$ represents an alkyl, cycloalkyl, heterocycloalkyl or phenyl group. Advantageously, $R_1$ represents a cycloalkyl group, such as a cyclohexyl group.

Among the compounds of formula (I) that are subjects of the invention, mention may also be made of those in which $R_a$, $R_{a'}$, $R_1$, $R_3$, $R_4$ and $R_5$ are as defined above, and $R_2$ is chosen from the following groups: $-CO-R_{15}$, $-CO-NR_{16}R_{17}$, $-CO-NR_{15}-NR_{16}R_{17}$, $-CO$-aryl, $-CO$-heteroaryl, $-CO-(CH_2)_x-NR_{16}R_{17}$, $-(CH_2)_x-NR_{16}R_{17}$, $-(CH_2)_x-OH$, $-(CH_2)_x$-aryl, $-(CH_2)_x$-heteroaryl, $-(CH_2)_x-CO-R_{15}$ and $-(CH_2)_x-CO-NR_{16}R_{17}$, in which:

x=0, 1, 2, 3 or 4 and x'=1, 2, 3 or 4, $R_{15}$ represents a hydrogen atom, or an alkyl, cycloalkyl or alkoxy group, and $R_{16}$ and $R_{17}$, which may be identical to or different from one another, represent a hydrogen atom, or an alkyl, cycloalkyl or alkoxy group, or else $R_{16}$ and $R_{17}$ form, together with the nitrogen atom to which they are attached, a mono- or bicyclic structure containing from 4 to 10 ring members and optionally comprising 1 to 3 additional hetero atoms and/or 1 to 3 ethylenic or acetylenic unsaturations, this ring being optionally substituted in any positions with 1 to 3 groups chosen from halogen atoms, and hydroxyl, alkyl, cycloalkyl and alkoxy groups.

Among the compounds of formula (I) that are subjects of the invention, mention may more particularly be made of those in which $R_2$ represents a group $-CO-NR_{16}R_{17}$, where $R_{16}$ and $R_{17}$ represent alkyl or alkoxy groups. $R_2$ advantageously represents a group $-CO-NR_{16}R_{17}$, where $R_{16}$ and $R_{17}$ represent alkyl groups.

Among the compounds of formula (I) that are subjects of the invention, mention may also be made of those in which $R_a$, $R_{a'}$, $R_1$, $R_2$, $R_4$ and $R_5$ are as defined above and $R_3$ represents 1 to 3 groups, which may be identical to or different from one another, chosen from halogen atoms. Advantageously, $R_3$ represents a single group, preferably a chlorine atom.

Among the compounds of formula (I) that are subjects of the invention, mention may also be made of those in which $R_a$, $R_{a'}$, $R_1$, $R_2$, $R_3$ and $R_5$ are as defined above, and $R_4$ is chosen from:

(1) a group of formula (a-1), (a-2), (a-3), (a-4) or (b-1) below:

(a-1)

(a-2)

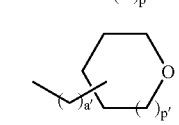

(a-3)

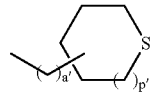

(a-4)

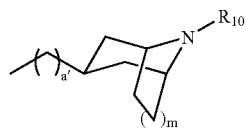

(b-1)

in which each of the rings of formulae (a-1), (a-2), (a-3), (a-4) and (b-1) can be substituted, in any positions, with 1 to 4 groups $R_7$, which may be identical to or different from one another, as defined above, and in which a'=0 or 1, p=0, 1, 2 or 3, p'=0 or 1, m=0, 1 or 2, and $R_6$ and $R_{10}$ are as defined above, (2) a group of formula $-A-R_{18}$ or $-A-CH=N-R_{19}$, where A, $R_{18}$ and $R_{19}$ are as defined above, (3) a group of formula (d) as defined above:

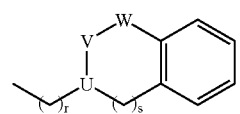

(d)

(4) a group $-(CH_2)_r$-furyl or $-(CH_2)_r$-pyridinyl, where r is equal to 1, 2 or 3.

In the groups of formulae (a-1), (a-2), (a-3), (a-4) or (b-1) above, mention may in particular be made of those for which $R_6$ represents an $-NH_2$ or phenyl group, $R_7$ represents a hydrogen atom or a hydroxyl group, and $R_{10}$ represents a hydrogen atom or an aryl or alkylaryl group, or forms, with the nitrogen atom to which it is attached and a carbon atom located in any position of the cyclic structure of formula (a-1), but not adjacent to said nitrogen atom, a bridge comprising from 3 to 5 members. Advantageously, $R_{10}$ represents a hydrogen atom in the group of formula (b-1) and, in the group of formula (a-1), a hydrogen atom or a phenyl or benzyl group, or forms, with the nitrogen atom to which it is attached and a carbon atom located in any position of the cyclic structure of formula (a-1), but not adjacent to said nitrogen atom, a bridge comprising 4 members.

Among the compounds of formula (I) that are subjects of the invention, mention may also be made of those in which $R_a$, $R_{a'}$, $R_1$, $R_2$, $R_3$ and $R_5$ are as defined above, and $R_4$ is chosen from:

(1) a group of formula (a-5), (a-6) or (b-2) below:

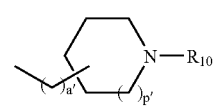

(a-5)

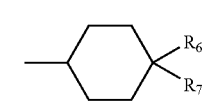

(a-6)

-continued

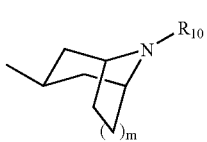

(b-2)

in which each of the rings of formulae (a-5), (a-6) and (b-2) can be substituted, in any positions, with 1 to 4 groups $R_7$, which may be identical to or different from one another, as defined above, and in which a'=0 or 1, p'=0 or 1, m=0, 1 or 2, and $R_6$ and $R_{10}$ are as defined above, (2) a group of formula -A-$R_{18}$ or -A-CH=N—$R_{19}$, where A, $R_{18}$ and $R_{19}$ are as defined above, (3) a group of formula (d-1), where r=1, 2 or 3:

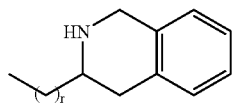

(d-1)

(4) a group —(CH$_2$)$_r$-furyl or —(CH$_2$)$_r$-pyridinyl, where r is equal to 1, 2 or 3.

In the groups of formulae (a-5), (a-6) and (b-2) above, mention may in particular be made of those for which $R_6$ represents an —NH$_2$ or phenyl group, $R_7$ represents a hydrogen atom or a hydroxyl group, and $R_{10}$ represents a hydrogen atom or an aryl or alkylaryl group, or forms, with the nitrogen atom to which it is attached and a carbon atom located in any position of the cyclic structure of formula (a-5), but not adjacent to said nitrogen atom, a bridge comprising from 3 to 5 members. Advantageously, $R_{10}$ represents a hydrogen atom in the group of formula (b-2) and, in the group of formula (a-5), a hydrogen atom or a phenyl or benzyl group, or forms, with the nitrogen atom to which it is attached and a carbon atom located in any position of the cyclic structure of formula (a-5), but not adjacent to said nitrogen atom, a bridge comprising 4 members.

Among the compounds of formula (I) that are subjects of the invention, mention may also be made of those in which $R_a$, $R_{a'}$, $R_1$, $R_2$, $R_3$ and $R_4$ are as defined above and $R_5$ represents a hydrogen atom or an alkyl group comprising from 1 to 4 carbon atoms. $R_5$ preferably represents a hydrogen atom.

Among the compounds of formula (I) that are subjects of the invention, mention may also be made of those in which $R_1$, $R_2$, $R_3$, $R_4$ and $R_5$ are as defined above, and $R_a$ and $R_{a'}$ represent hydrogen atoms or alkyl groups comprising from 1 to 4 carbon atoms. Advantageously, $R_a$ and $R_{a'}$ represent, independently of one another, hydrogen atoms or methyl groups. Preferably, $R_a$=$R_{a'}$=H.

Among the groups $R_6$ defined above, mention may in particular be made of those in which $R_6$ represents a hydrogen atom or an —NR$_8$R$_9$ or aryl group, in which $R_8$ and $R_9$ represent a hydrogen atom or an alkyl group. Mention may also be made of the groups $R_6$ representing a hydrogen atom or an —NH$_2$ or phenyl group.

Among the groups $R_7$ defined above, mention may in particular be made of those in which $R_7$ represents a hydrogen or halogen atom, or an alkyl group, hydroxyl group (corresponding to a group —OR, where R represents a hydrogen atom) or alkoxy group (corresponding to a group —OR, where R represents an alkyl group). $R_7$ advantageously represents a hydrogen atom or a hydroxyl group.

Among the groups $R_8$ and $R_9$ defined above, mention may in particular be made of those in which $R_8$ and $R_9$ represent a hydrogen atom or an alkyl group.

Among the groups $R_{10}$ defined above, mention may in particular be made of those in which $R_{10}$ represents a hydrogen atom, or an aryl group (such as a phenyl group) or alkylaryl group (such as a benzyl group), or else $R_{10}$ forms, with the nitrogen atom that carries it and a carbon atom located in any position of the cyclic structure to which it is attached, but not adjacent to said nitrogen atom, a bridge comprising from 3 to 5 members.

Among the groups R and R' defined above, mention may in particular be made of those in which R and R' represent a hydrogen atom or an alkyl group.

Each of the definitions given above for the groups $R_a$, $R_{a'}$, $R_1$, $R_2$, $R_3$, $R_4$, $R_5$, $R_6$, $R_7$, $R_8$, $R_9$, $R_{10}$, R and R' can be combined with one another so as to obtain various subgroups of compounds of formula (I) according to the present invention.

Mention may, for example, be made of a subgroup of compounds of formula (I) according to the invention, in which:

$R_a$ and $R_{a'}$ represent, independently of one another, hydrogen atoms or methyl groups, $R_1$ represents an alkyl, cycloalkyl or heterocycloalkyl group, $R_2$ is chosen from the following groups: —CO—$R_{15}$, —CO—NR$_{16}$R$_{17}$, —CO—NR$_{15}$—NR$_{16}$R$_{17}$, —CO-aryl, —CO-heteroaryl, —CO—(CH$_2$)$_x$—NR$_{16}$R$_{17}$, —(CH$_2$)$_x$—NR$_{16}$R$_{17}$, —(CH$_2$)$_x$—OH, —(CH$_2$)$_x$-aryl, —(CH$_2$)$_x$-heteroaryl, —(CH$_2$)$_x$—CO—$R_{15}$ and —(CH$_2$)$_{x'}$—CO—NR$_{16}$R$_{17}$, in which:

x=0, 1, 2, 3 or 4 and x'=1, 2, 3 or 4, $R_{15}$ represents a hydrogen atom, or an alkyl, cycloalkyl or alkoxy group, and $R_{16}$ and $R_{17}$, which may be identical to or different from one another, represent a hydrogen atom, or an alkyl, cycloalkyl or alkoxy group, or else $R_{16}$ and $R_{17}$ form, together with the nitrogen atom to which they are attached, a mono- or bicyclic structure containing from 4 to 10 ring members and optionally comprising 1 to 3 additional hetero atoms and/or 1 to 3 ethylenic or acetylenic unsaturations, this ring being optionally substituted in any positions with 1 to 3 groups chosen from halogen atoms, and hydroxyl, alkyl, cycloalkyl and alkoxy groups, $R_3$ represents 1 to 3 groups, which may be identical to or different from one another, chosen from halogen atoms, $R_4$ is chosen from:

(1) a group of formula (a-1), (a-2), (a-3), (a-4), or (b-1) below:

(a-1)

(a-2)

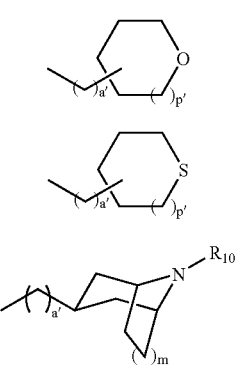

in which each of the rings of formulae (a-1), (a-2), (a-3), (a-4) and (b-1) may be substituted, in any positions, with 1 to 4 groups $R_7$ which may be identical to or different from one another, as defined above, and in which a'=0 or 1, p=0, 1, 2 or 3, p'=0 or 1, m=0, 1 or 2, and $R_6$ and $R_{10}$ are as defined above, (2) a group of formula $-A-R_{18}$ or $-A-CH=N-R_{19}$, where A, $R_{18}$ and $R_{19}$ are as defined above, (3) a group of formula (d) as defined above:

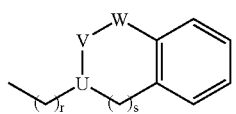

(4) a group $-(CH_2)_r$-furyl or $-(CH_2)_r$-pyridinyl, where r is equal to 1, 2 or 3, and $R_5$ represents a hydrogen atom.

According to another subject, the invention relates to the preferred compounds, in particular the compounds of endo configuration, having the following names:

In the lists that follow, the numbers in front of the names of the products correspond to the example Nos. of the compounds in the table:

1: N-[8-(4-chloro-N-piperidin-4-yl-D-phenylalanyl)-8-azabicyclo[3.2.1]oct-3-yl]-N-cyclohexyl-N',N'-diethylurea 2: N-[8-(4-chloro-N-piperidin-3-yl-D-phenylalanyl)-8-azabicyclo[3.2.1]oct-3-yl]-N-cyclohexyl-N',N'-diethylurea 3: N-{8-[N-(4-aminocyclohexyl)-4-chloro-D-phenylalanyl]-8-azabicyclo[3.2.1]oct-3-yl}-N-cyclohexyl-N',N'-diethylurea 4: N-{8-[4-chloro-N-(tetrahydro-2H-pyran-4-yl)-D-phenylalanyl]-8-azabicyclo[3.2.1]oct-3-yl)-N-cyclohexyl-N',N'-diethylurea 5: N-[8-(N-8-azabicyclo[3.2.1]oct-3-yl-4-chloro-D-phenylalanyl)-8-azabicyclo[3.2.1]oct-3-yl]-N-cyclohexyl-N',N'-diethylurea 6: N-{8-[4-chloro-N-(piperidin-4-ylmethyl)-D-phenylalanyl]-8-azabicyclo[3.2.1]oct-3-yl}-N-cyclohexyl-N',N'-diethylurea 7: N-{8-[4-chloro-N-(piperidin-2-ylmethyl)-D-phenylalanyl]-8-azabicyclo[3.2.1]oct-3-yl}-N-cyclohexyl-N',N'-diethylurea 8: N-{8-[4-chloro-N-(tetrahydro-3-thienyl)-D-phenylalanyl]-8-azabicyclo[3.2.1]oct-3-yl}-N-cyclohexyl-N',N'-diethylurea 9: N-[8-(N-1-azabicyclo[2.2.2]oct-3-yl-4-chloro-D-phenylalanyl)-8-azabicyclo[3.2.1]oct-3-yl]-N-cyclohexyl-N',N'-diethylurea 10: N-[8-(N-azepan-4-yl-4-chloro-D-phenylalanyl)-8-azabicyclo[3.2.1]oct-3-yl]-N-cyclohexyl-N',N'-diethylurea 11: N-[8-(4-chloro-N-([(2S,4R)-4-hydroxypyrrolidin-2-yl]methyl}-D-phenylalanyl)-8-azabicyclo[3.2.1]oct-3-yl]-N-cyclohexyl-N',N'-diethylurea 12: N-[8-(4-chloro-N-([{2R,4R)-4-hydroxypyrrolidin-2-yl]methyl}-D-phenylalanyl)-8-azabicyclo[3.2.1]oct-3-yl]-N-cyclohexyl-N',N'-diethylurea 13: N-[8-(4-chloro-N-{[(2R,4S)-4-hydroxypyrrolidin-2-yl]methyl}-D-phenylalanyl)-8-azabicyclo[3.2.1]oct-3-yl]-N-cyclohexyl-N',N'-diethylurea 14: N-{8-[4-chloro-N-(1-phenylpiperidin-4-yl)-D-phenylalanyl]-8-azabicyclo[3.2.1]oct-3-yl}-N-cyclohexyl-N',N'-diethylurea 15: N-(8-{N-[(1-benzylpyrrolidin-3-yl)methyl]-4-chloro-D-phenylalanyl}-8-azabicyclo[3.2.1]oct-3-yl)-N-cyclohexyl-N',N'-diethylurea 16: N-[8-(4-chloro-N-pyrrolidin-3-yl-D-phenylalanyl)-8-azabicyclo[3.2.1]oct-3-yl]-N-cyclohexyl-N',N'-diethylurea 17: N-(8-{4-chloro-N-[4-(4-hydroxyphenyl)cyclohexyl]-D-phenylalanyl}-8-azabicyclo[3.2.1]oct-3-yl)-N-cyclohexyl-N',N'-diethylurea 18: N-{8-[N-(2-aminoethyl)-4-chloro-D-phenylalanyl]-8-azabicyclo[3.2.1]oct-3-yl}-N-cyclohexyl-N',N'-diethylurea 19: N-{8-[N-(3-aminopropyl)-4-chloro-D-phenylalanyl]-8-azabicyclo[3.2.1]oct-3-yl}-N-cyclohexyl-N',N'-diethylurea 20: N-(8-{4-chloro-N-[(2E)-2-(hydroxyimino)-1-methylethyl]-D-phenylalanyl}-8-azabicyclo[3.2.1]oct-3-yl)-N-cyclohexyl-N',N'-diethylurea 21: N-{[8-[4-chloro-N-(2-fluoro-1-methylethyl)-D-phenylalanyl]-8-azabicyclo[3.2.1]oct-3-yl}-N-cyclohexyl-N',N'-diethylurea 22: N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea 23: N-{8-[4-chloro-N-(pyridin-2-ylmethyl)-D-phenylalanyl]-8-azabicyclo[3.2.1]oct-3-yl}-N-cyclohexyl-N',N'-diethylurea 24: N-{8-[4-chloro-N-(2-furylmethyl)-D-phenylalanyl]-8-azabicyclo[3.2.1]oct-3-yl}-N-cyclohexyl-N',N'-diethylurea 25: N-(8-{4-chloro-N-[(2R)-pyrrolidin-2-ylmethyl]-D-phenylalanyl}-8-azabicyclo[3.2.1]oct-3-yl)-N-cyclohexyl-N',N'-diethylurea 26: N-(8-{4-chloro-N-[(2S)-pyrrolidin-2-ylmethyl]-D-phenylalanyl}-8-azabicyclo[3.2.1]oct-3-yl)-N-cyclohexyl-N',N'-diethylurea 27: N-[8-(N-azetidin-3-yl-4-chloro-D-phenylalanyl)-8-azabicyclo[3.2.1]oct-3-yl]-N-cyclohexyl-N',N'-diethylurea 28: N-(8-{N-[(1-benzylpyrrolidin-3-yl)methyl]-4-chloro-D-phenylalanyl}-8-azabicyclo[3.2.1]oct-3-yl)-N-cyclohexyl-N',N'-diethylurea In the subsequent text, the term "protective group (Pg)" is intended to mean a group which makes it possible, firstly, to protect a reactive function such as a hydroxyl or an amine during a synthesis and, secondly, to regenerate the intact reactive function at the end of synthesis. Examples of protective groups and also of methods of protection and of deprotection are given in "Protective Groups in Organic Synthesis", Green W. et al., 1999, 3rd Edition (John Wiley & Sons, Inc., New York).

In the subsequent text, the term "leaving group (Lg)" is intended to mean a group that can be readily cleaved from a molecule by heterolytic bond breaking, resulting in a pair of electrons leaving. This group can thus be readily replaced with another group in a substitution reaction, for example. Such leaving groups are, for example, halogens or an activated hydroxyl group such as a mesyl, tosyl, triflate, acetyl, etc. Examples of leaving groups and also references for the preparation thereof are given in "March's Advanced Organic Chemistry", J. March et al., 5$^{th}$ Edition, 2001, EMInter publisher.

The term "Boc group" is intended to mean a t-butoxycarbonyl group, "Bn group" is intended to mean a benzyl group, "CBz group" is intended to mean a benzyloxycarbonyl group, "Fmoc group" is intended to mean a 9-fluorenylmethylcarbamate group, and the term "h" is intended to mean hours.

In accordance with the invention, the compounds of general formula (I) can be prepared according to the method presented in scheme 1.

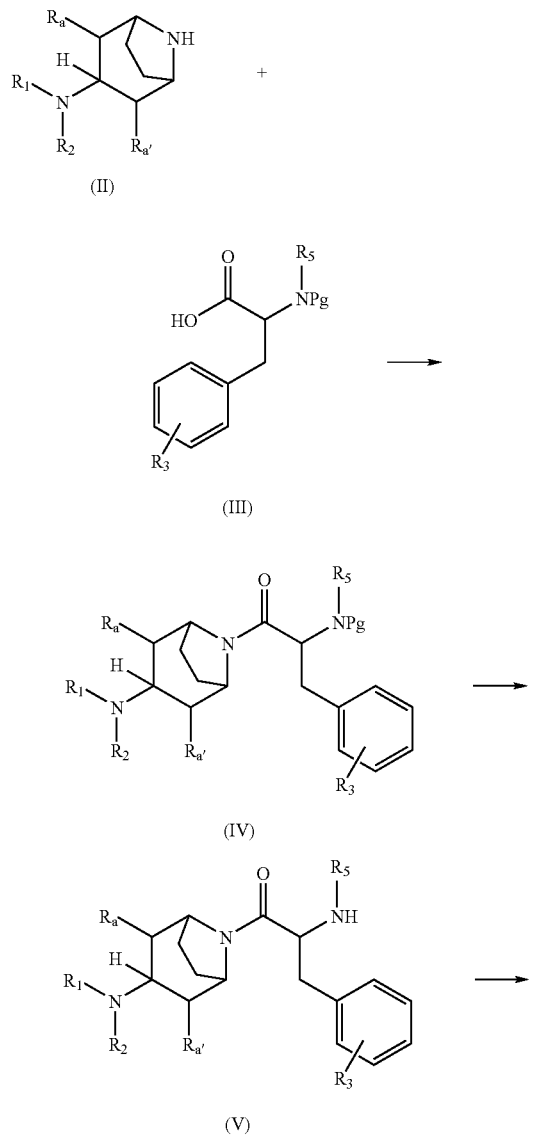

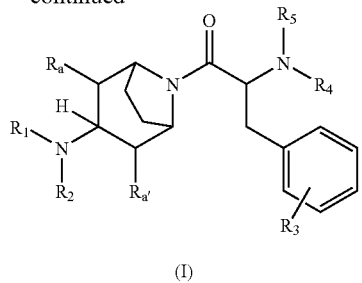

According to scheme 1, the compounds of formula (IV) can be prepared by coupling between the intermediates of formula (II) and an amino acid of formula (III), the amine function of which is protected with a protective group Pg (for example, a Boc, CBz, Bn or Fmoc group), under conventional peptide coupling conditions, using, for example, as coupling agent, dicyclocarbodiimide, 1-(3-dimethylaminopropyl)-3-ethylcarbodiimide hydrochloride or bromotrispyrrolidinophosphonium hexafluorophosphate, possibly in the presence of hydroxybenzotriazole, and, as base, triethylamine or diisopropylethylamine in a solvent such as dioxane, dichloromethane or acetonitrile.

The amino acids of general formula (III) are commercially available or can be prepared by methods described in the literature (Williams, R. M., Synthesis of Optically Active □-Aminoacids, Pergamon Press, Oxford, 1989).

The compounds of formula (V) are obtained by deprotection of the amine function of the compounds of formula (IV), by methods chosen from those known to those skilled in the art. They comprise, inter alia, the use of trifluoroacetic acid or hydrochloric acid in dichloromethane, dioxane, tetrahydrofuran or diethyl ether in the case of a protection with a BOC group, hydrogenation with the appropriate metal in methanol or ethanol in the case of a CBz, and of piperidine for an Fmoc group., at temperatures ranging from −10° C. to 100° C.

In a final step, the compounds of formula (I) are obtained by reductive amination, carried out by bringing the compounds of formula (V) into contact with a derivative of the group $R_4$ of oxo (aldehyde or ketone) type, using a reducing agent such as sodium borohydride, sodium triacetoxyborohydride or sodium cyanoborohydride, possibly in the presence of a Brønsted acid (such as hydrochloric acid) or a Lewis acid (such as titanium tetraisopropoxide) in a solvent such as dichloroethane, dichloromethane, acetic acid or methanol, at temperatures of between −10° C. and 30° C. The aldehydes derived from the group $R_4$, when they are not commercial, are prepared from the corresponding acids by methods known to those skilled in the art, for example by conversion to Weinreb amides under peptide coupling conditions, and then by reduction thereof with a hydride such as lithium aluminium hydride.

The derivatives of the group $R_4$ of ketone or aldehyde type may be commercial or may be obtained by methods known to those skilled in the art, for example by acylation of the free hydroxyl or amine function of the derivative of ketone type.

The compounds of general formula (I), in which $R_4$ corresponds to formulae (a), (b), (c), (d), -A-$R_{18}$, -A-N($R_{20}$)-A'-$R_{19}$ and -A-CH(NH$_2$)—$R_{19}$, can also be prepared according to the method presented in scheme 2.

Scheme 2:

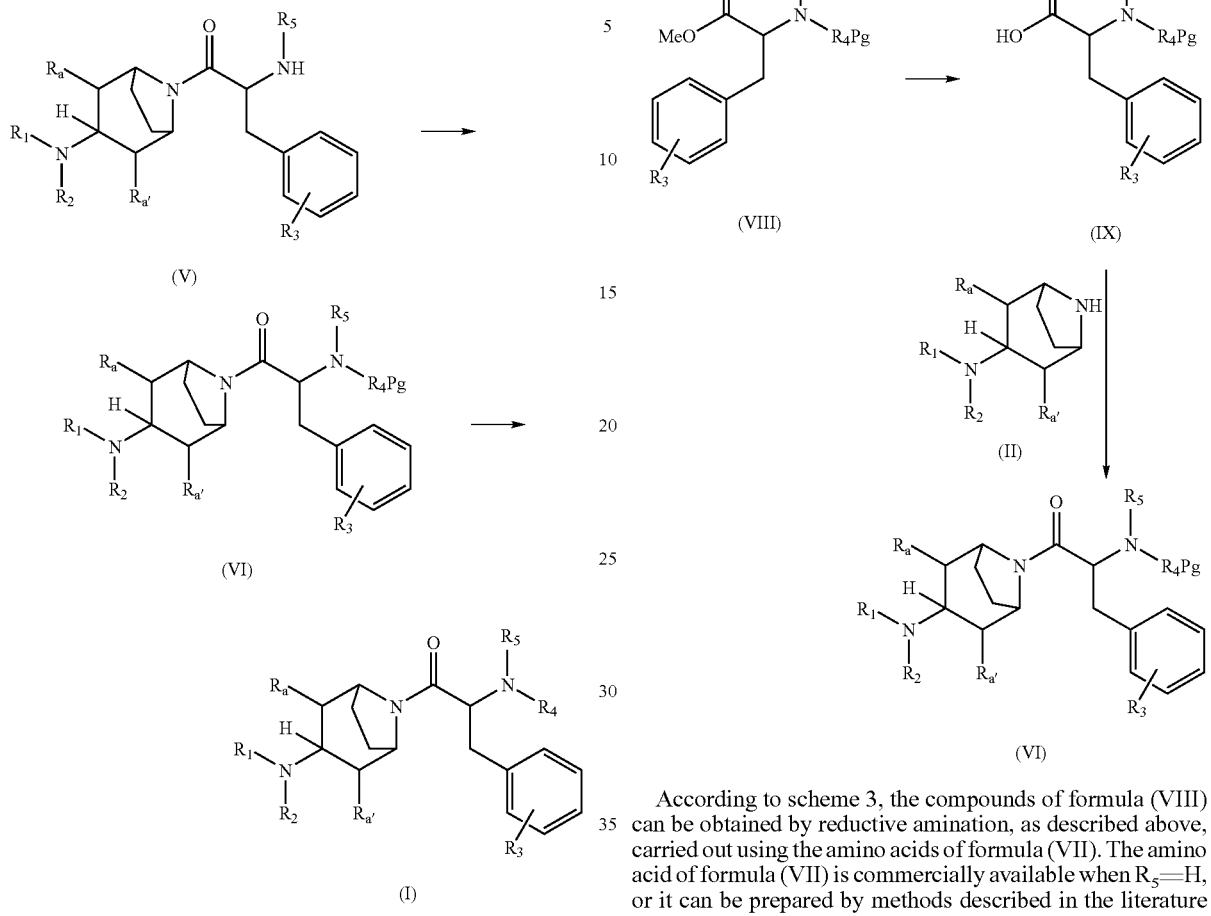

According to scheme 2, the compounds of formula (V), obtained as described above in scheme 1, are brought into contact with a derivative of the group $R_4$ of oxo type (reductive amination reaction, as described above in relation to scheme 1), said group $R_4$ bearing an amine-protecting group Pg, to give the compounds of formula (VI). The amine function of the compounds of formula (VI) is then deprotected by methods known to those skilled in the art, as described above.

Alternatively, the compounds of formula (VI) that give the compounds of formula (I) can be prepared according to the method presented in scheme 3.

Scheme 3:

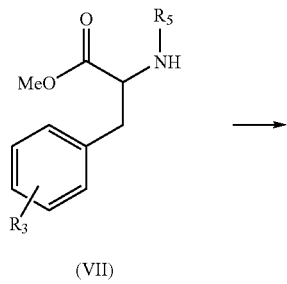

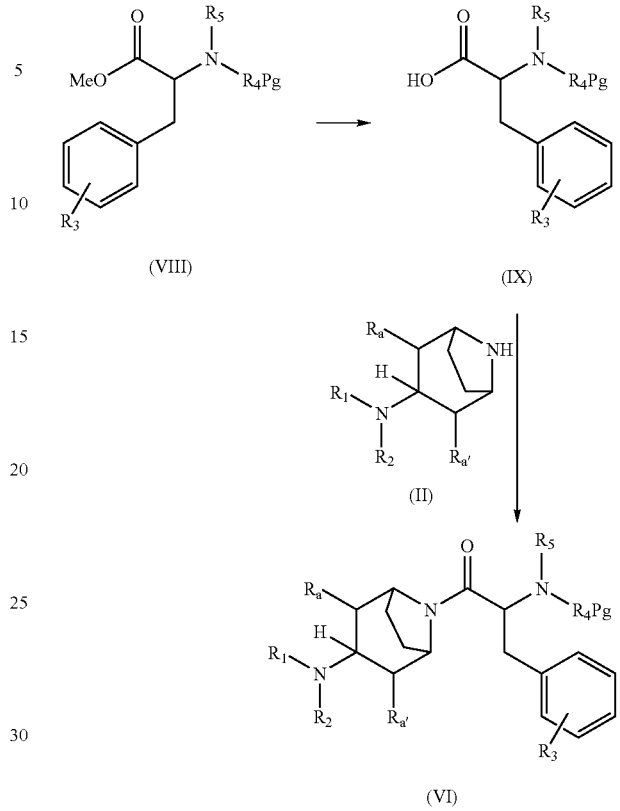

According to scheme 3, the compounds of formula (VIII) can be obtained by reductive amination, as described above, carried out using the amino acids of formula (VII). The amino acid of formula (VII) is commercially available when $R_5$=H, or it can be prepared by methods described in the literature (Williams, R. M., Synthesis of Optically Active □-Aminoacids, Pergamon Press, Oxford, 1989). When $R_5$ represents an alkyl group, the amino acids of formula (VII) can be prepared by alkylation of the commercial amino acid protected on the amine function, according to the alkylation methods known to those skilled in the art.

The compounds of formula (IX) can be synthesized by saponification of the esters of formula (VIII), for example in the presence of sodium hydroxide or of lithium hydroxide in a solvent such as methanol, tetrahydrofuran or water, or a mixture of these solvents.

The compounds of formula (VI) can be prepared by peptide coupling between the intermediates of formula (II) and the amino acid of formula (IX), under conventional peptide coupling conditions as described in scheme 1.

The compounds of formula (II) can be obtained according to the method presented in scheme 4.

Scheme 4:

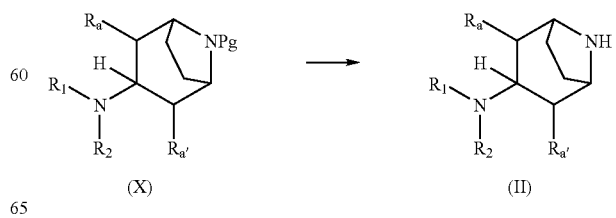

According to scheme 4, the compounds of formula (II) can be prepared from the compound of formula (X) (where Pg is an amine-protecting group as defined in scheme 1), after deprotection of the amine function by methods chosen from those known to those skilled in the art, as described above.

The compound of formula (X) is prepared according to the methods described in the literature or known to those skilled in the art, adapted according to the nature of the groups $R_1$ and $R_2$. Schemes 5 to 9 below present examples of preparation of the compounds of formula (X) according to various natures of the groups $R_2$. For example, when $R_2$ represents a group —CO—$R_{15}$, where $R_{15}$ is as defined above, the preparation of the corresponding compound (Xa) can be carried out according to scheme 5.

which is protected (for example, commercial Boc-nortropanone). The compounds of formula (Xa) are then obtained by reaction of the compounds of formula (XI) with an acid chloride of formula $R_{15}$COCl, in the presence of an organic base such as triethylamine or pyridine, in a solvent such as dichloromethane or tetrahydrofuran.

Scheme 6 presents a pathway for preparing the compounds of formulae (Xb) and (Xc), which correspond respectively to the compounds of formula (X) in which $R_2$ represents a group —CO—$NR_{16}R_{17}$ and —CO—$NR_{15}$—$NR_{16}R_{17}$, where $R_{15}$, $R_{16}$ and $R_{17}$ are as defined above.

Scheme 6:

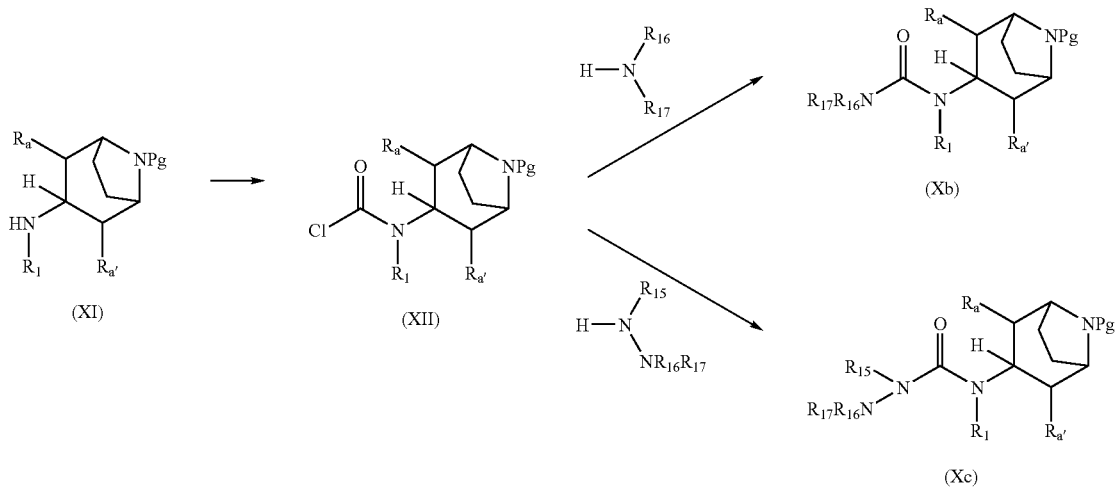

According to scheme 6, the compounds of formula (XII) can be prepared from the compounds of formula (XI) by reaction with phosgene, triphosgene or trichloromethyl chloroformate in dichloromethane or toluene in the presence of triethylamine or of pyridine and an amine at temperatures ranging from −10° C. to 80° C. The reaction of the compounds of formula (XII) with an amine of formula HN($R_{16}$)($R_{17}$) or a hydrazine of formula HN($R_{15}$)($NR_{16}R_{17}$) results, respectively, in the compounds of formulae (Xb) and (Xc).

Scheme 7 presents a pathway for preparing the compounds of formula (Xd), corresponding to the compounds of formula (X) in which $R_2$ represents a group —$(CH_2)_x$—$NR_{16}R_{17}$, where x=2, 3 or 4 and $R_{16}$ and $R_{17}$ are as defined above.

Scheme 5:

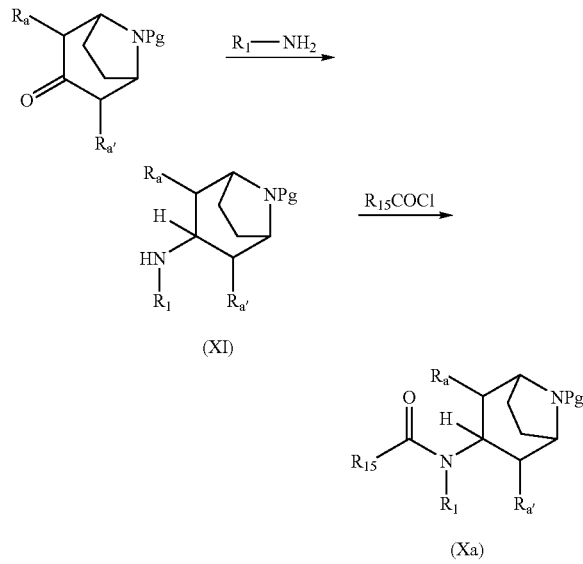

According to scheme 5, the compounds of formula (XI) can be obtained by reductive amination, under the conditions described above, of nortropanone, the amine function of Scheme 7:

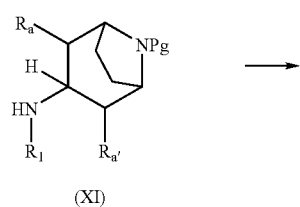

-continued

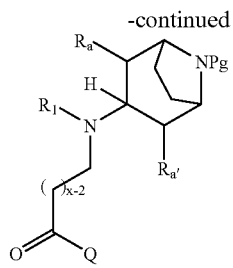
(XIII)

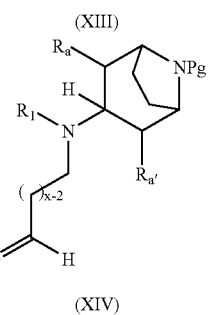
(XIV)

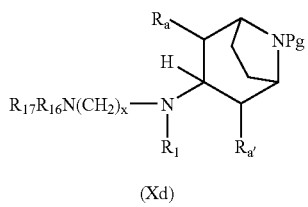
(Xd)

According to scheme 7, the compounds of formula (XIII) can be obtained by reductive amination performed on the compounds of formula (XI) in the presence of an aldehyde of formula Q-CO—$(CH_2)_{x-2}$—CHO, where Q represents an —O-alkyl or —N(O-alkyl)(alkyl) group, using a reducing agent as described above in relation to scheme 1.

The compounds of general formula (XIII) can then be reduced to give the aldehydes of formula (XIV), using a reducing agent such as diisobutylaluminium hydride or sodium aluminium tetrahydride when Q is an —O-alkyl group, or by reduction with lithium aluminium hydride when Q is an —N(O-alkyl)(alkyl) group (for example, —N(OMe)Me), obtained for example by reaction of an organomagnesium compound, such as diisopropyl magnesium chloride with the compounds of formula (XIII) where Q=—O-alkyl, in the presence of an alkylhydroxyalkylamine such as N,O-dimethylhydroxylamine, in solvents such as tetrahydrofuran or diethyl ether at temperatures ranging from −78° C. to 20° C.

The compounds of formula (Xd) can then be prepared by reductive amination carried out in the presence of an amine of formula $R_{17}R_{16}NH$, using a reducing agent as described above.

Scheme 8 presents a pathway for preparing the compounds of formula (Xe), corresponding to the compounds of formula (X) in which $R_2$ represents a group —$(CH_2)_x$-aryl (where x=0, 1, 2, 3 or 4) or —$(CH_2)_x$-heteroaryl (where x=1, 2, 3 or 4).

Scheme 8:

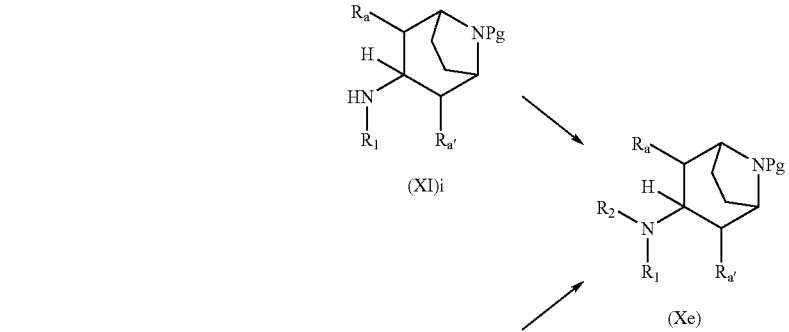

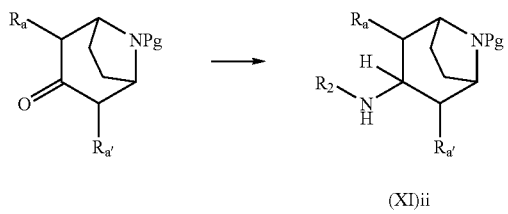

According to scheme 8, the compounds of formulae (Xe) in which $R_2$ represents a group —$(CH_2)_x$-heteroaryl (where x=1, 2 or 3) can be obtained by reductive amination using the compounds of formula (XI)i, carried out in the presence of an aldehyde of formula: heteroaryl-$(CH_2)_{x-1}$—CHO, using a reducing agent as described above in relation to scheme 1.

The same reaction can also be carried out so as to obtain the compounds of formula (Xd), using an aldehyde of formula $R_{17}R_{16}N$—$(CH_2)_{x-1}$—CHO.

The compounds of formulae (XI)ii in which $R_2$ represents a group —$(CH_2)_x$-aryl (where x=0, 1, 2 or 3) can be obtained by reductive amination using nortropanone protected on the amine function (such as Boc-nortropanone), carried out in the presence of an amine of formula: aryl-$(CH_2)_x$—$NH_2$, using a reducing agent as described above in relation to scheme 1. The compounds of formulae (Xe) in which $R_2$ represents a group —$(CH_2)_x$-aryl can then be obtained by reductive amination using the compounds of formula (XI)ii, carried out in the presence of a derivative of group $R_1$ of oxo type.

Scheme 9 gives the details of an alternative for synthesizing the compounds of formula (Xe) in which $R_2$ represents a group —$(CH_2)_x$-heteroaryl, where x is equal to 2 or 3.

Scheme 9:

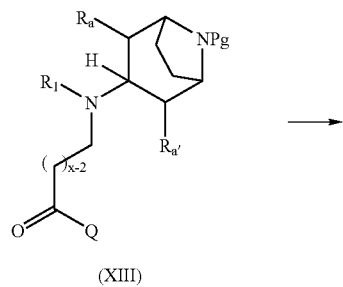

(XIII)

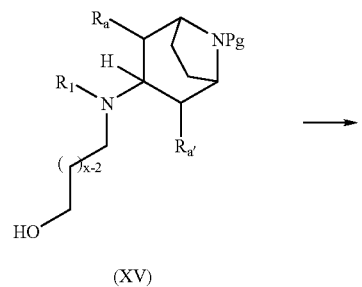

(XV)

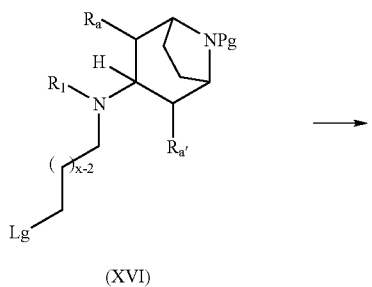

(XVI)

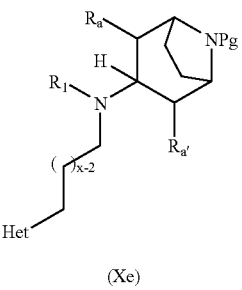

(Xe)

According to scheme 9, the compounds of formula (XIII), in which Q represents an —O-alkyl group, can be reduced to the corresponding alcohols using a reducing agent such as lithium aluminium hydride in a solvent such as diethyl ether or tetrahydrofuran, at temperatures ranging from −60° C. to 20° C.

The hydroxyl group of the compounds of formula (XV) is then converted to a leaving group (Lg), such as chloride or mesylate, for example by the action of tetrabromomethane and of triphenylphosphine in a solvent such as dichloromethane, or by the action of methanesulphonyl chloride in the presence of an organic base such as triethylamine, at temperatures ranging from −20° C. to ambient temperature, to give the compounds of formula (XVI).

The compounds of formula (Xe) are then synthesized by means of a nucleophilic substitution reaction between the compounds of formula (XVI) and the anion of a heteroaryl ("Het" group).

Scheme 10 presents a pathway for preparing the compounds of formula (I), in which $R_4$ represents a group of formula (d) as defined above, where r=1, 2 or 3, s=1 and U represents a nitrogen atom.

Scheme 10:

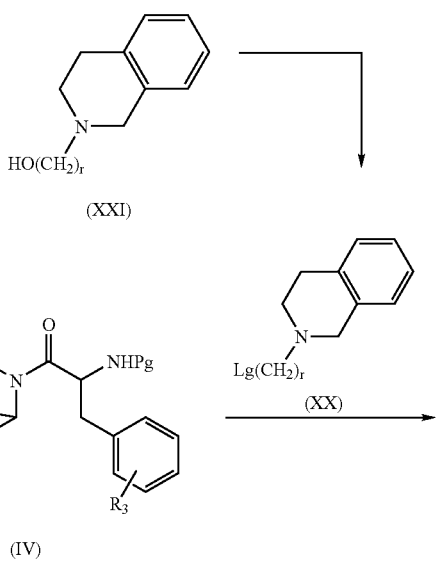

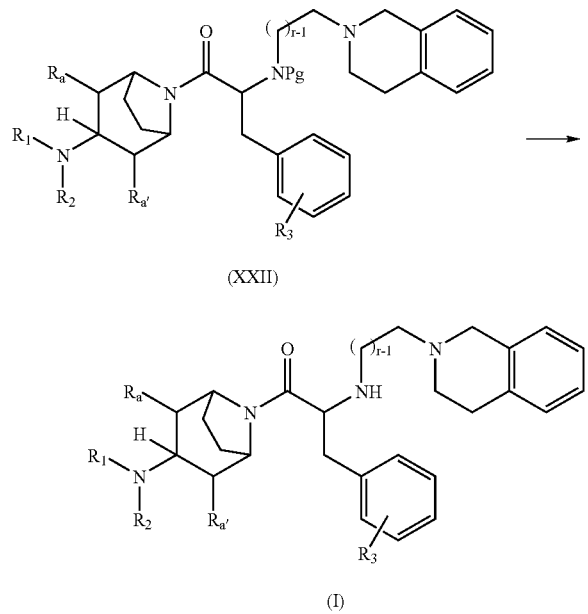

(XXII)

(I)

The compounds of formula (XXII) can be obtained by alkylation of the compounds of formula (IV) [where $R_5$=H] with tetrahydroisoquinolines of formula (XX), substituting the leaving group (Lg) of the compounds of formula (XX) with the anion of the compounds of formula (IV), formed by reaction with sodium hydride in a solvent such as dimethylformamide at temperatures ranging from −20° C. to 60° C., or by reaction with lithium diisopropylamide in a solvent such as tetrahydrofuran or diethyl ether at temperatures ranging from −78° C. to 25° C.

The compounds of formula (XX) are prepared under conventional conditions, such as by conversion of the hydroxyl group of the compounds of formula (XXI) into a leaving group, such as chloride or mesylate, for example by the action of tetrabromomethane and of triphenylphosphine in a solvent such as dichloromethane, or by the action of methanesulphonyl chloride in the presence of an organic base such as triethylamine at temperatures ranging from −20° C. to ambient temperature. The compounds of formula (XXI) are synthesized according to the methods of alkylation known to those skilled in the art from commercial 1,2,3,4-tetrahydroisoquinoline.

The amine function of the compounds of formula (XII) is deprotected, under conditions as described in scheme 1, so as to give the compounds of formula (I) [where $R_5$=H and $R_4$=2-alkyl-1,2,3,4-tetrahydroisoquinoline].

According to a variant of scheme 1, when the compounds of formula (I) comprise, as group $R_4$, a group of formula (a) of cyclohexyl type, i.e. a group of formula (a) where a=0, p=2 and X=—C($R_6$)($R_7$)—, where $R_6$ represents a group —$OR_8$, $R_7$ and $R_8$ being as defined above, then the preparation of the compounds of formula (I) can be carried out as described in Scheme 11:

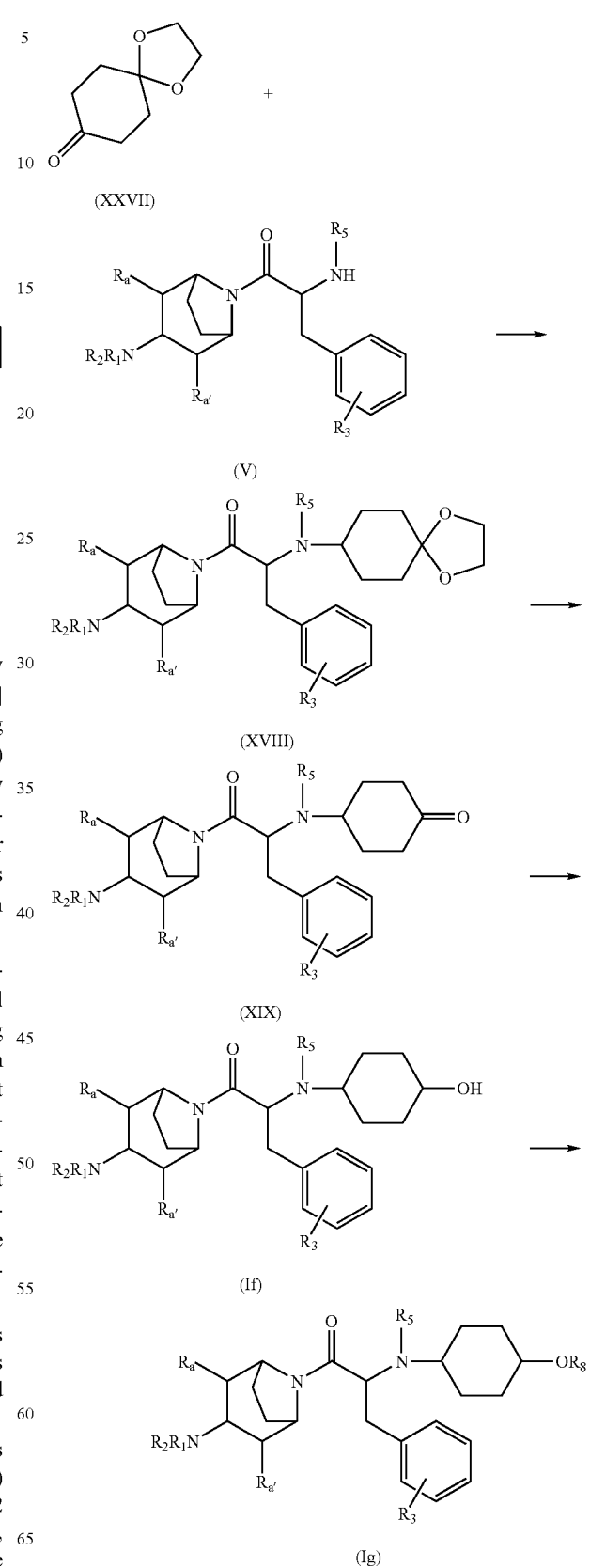

(XXVII)

(V)

(XVIII)

(XIX)

(If)

(Ig)

According to scheme 11, the compounds of formula (XVIII) can be obtained by reductive amination between the commercial compound of formula (XVII) and the compounds of formula (V), under conditions as described in scheme 1.

Deprotection of the oxo function of the compound of formula (XVIII) in the presence of an acid such as hydrochloric acid or pyridinium tosylate in tetrahydrofuran or acetone at temperatures of between 0° C. and 80° C., gives the compound of formula (XIX).

The compounds of formula (If) are prepared by reduction of the compounds of formula (XIX) under conditions as described in scheme 6.

When $R_8$ is different from a hydrogen atom, functionalization of the compounds of formula (If) is carried out, for example an alkylation in the presence of a base such as sodium hydride and of a derivative of the group $R_8$ comprising a leaving group Lg, which gives the compounds of formula (Ig).

In schemes 1 to 11, the starting compounds and the reactants, when the method for preparing them is not described, are commercially available or are described in the literature, or else can be prepared according to methods which are described therein or which are known to those skilled in the art.

According to another of its aspects, a subject of the invention is also the compounds of formulae (II), (IV), (V), (VI), (VIII), (IX), (X), (XVIII) and (XIX): these compounds are useful as synthesis intermediates for the compounds of formula (I).

The following examples describe the preparation of certain compounds in accordance with the invention. These examples are not limiting and merely illustrate the present invention. The numbers of the compounds exemplified refer to those given in the table hereinafter, which illustrates the chemical structures and the physical properties of some compounds according to the invention.

EXAMPLE 1

N-[8-(4-chloro-N-piperidin-4-yl-D-phenylalanyl)-8-azabicyclo[3.2.1]oct-3-yl]-N-cyclohexyl-N',N'-diethylurea (Compound No. 1)

1.1: tert-butyl 3-(cyclohexylamino)-8-azabicyclo[3.2.1]octane-8-carboxylate 9.1 g of cyclohexylamine and 10.3 g of Boc-nortropinone are dissolved in 150 ml of ethanol. 14.3 g of titanium tetraisopropoxide are added at ambient temperature. The reaction medium is stirred for 16 h. 2.6 g of sodium borohydride are added, fractionwise, at 0° C., and the reaction medium is then stirred at ambient temperature for 2 hours. After the addition of 50 ml of water and of 20 ml of aqueous ammonia (28% in water), the white precipitate formed in the reaction medium is filtered off over a bed of celite. The solid is washed several times with dichloromethane. The organic phases are then combined, washed with water, dried over $MgSO_4$ and concentrated. The crude obtained is chromatographed on silica gel, elution being carried out with a gradient of methanol in dichloromethane ranging from 0% to 10%. 7.7 g of tert-butyl 3-(cyclohexylamino)-8-azabicyclo[3.2.1]octane-8-carboxylate endo compound and 1.2 g of tert-butyl 3-(cyclohexylamino)-8-azabicyclo[3.2.1]octane-8-carboxylate exo compound are obtained. The subsequent synthesis concerns the endo compound.

1.2: tert-butyl 3-{cyclohexyl[(diethyl-amino)carbonyl]amino}-8-azabicyclo[3.2.1]octane-8-carboxylate 0.64 ml of diphosgene is placed in 10 ml of dichloromethane at 0° C. under $N_2$. A solution of 1.0 g of tert-butyl 3-(cyclohexylamino)-8-azabicyclo[3.2.1]-octane-8-carboxylate endo compound and 2.26 ml of triethylamine in 10 ml of dichloromethane is added dropwise. The solution is stirred at 0° C. for 30 min and then at ambient temperature for 4 h. 5 ml of triethylamine and 1.0 ml of diphosgene are then added. After stirring at ambient temperature for 2 h, 1.68 ml of diethylamine are added. The mixture is stirred at ambient temperature for 16 h. After concentration, 0.5N hydrochloric acid is added up to an acid pH. Extraction is carried out with dichloromethane until the aqueous phase is completely depleted. The organic phase is washed with $H_2O$, and then with a saturated aqueous sodium chloride solution. After drying over $MgSO_4$ and concentration to dryness, the residue obtained is chromatographed on silica gel, elution being carried out with a 99/1 and then 95/5 mixture of dichloromethane and methanol, to give 1.60 g of tert-butyl 3-{cyclohexyl[(diethylamino)carbonyl]amino}-8-azabicyclo[3.2.1]octane-8-carboxylate as a mixture with diethylurea.

1.3: N-8-azabicyclo[3.2.1]oct-3-yl-N-cyclohexyl-N', N'-diethylurea 3.0 g of tert-butyl 3-{cyclohexyl[(diethyl-amino)carbonyl]amino}-8-azabicyclo[3.2.1]octane-8-carboxylate mixed with diethylurea are placed in 37 ml of 2N hydrochloric acid in diethyl ether. The reaction medium is stirred at ambient temperature for 16 h. After evaporation to dryness, the residue is taken up with a 1N aqueous hydrochloric acid solution. Extraction is carried out with ethyl acetate and a 1N aqueous sodium hydroxide solution is then added up to a pH of 10. Extraction is carried out with ethyl acetate until the aqueous phase is completely depleted. The organic phase is washed with $H_2O$ and then with a saturated aqueous sodium chloride solution. After drying over $MgSO_4$ and concentration to dryness, 1.8 g of N-8-azabicyclo[3.2.1]oct-3-yl-N-cyclohexyl-N',N'-diethylurea are obtained.

1.4: tert-butyl [(1R)-1-(4-chlorobenzyl)-2-(3-{cyclohexyl[(diethylamino)carbonyl]amino}-8-azabicyclo [3.2.1]oct-8-yl)-2-oxoethyl]carbamate 1.8 g of N-8-azabicyclo[3.2.1]oct-3-yl-N-cyclohexyl-N', N'-diethylurea are dissolved in 70 ml of dichloromethane in the presence of 1.75 g of Boc-D-4-chlorophenylalanine, of 0.79 g of hydroxybenzotriazole, of 1.12 g of 1-(3-dimethylaminopropyl)-3-ethylcarbodiimide hydrochloride and of 1.02 ml of diisopropylethylamine. The mixture is stirred at ambient temperature for 16 h. After evaporation to dryness, the residue is hydrolysed and extracted with ethyl acetate until the aqueous phase is completely depleted. The organic phase is washed with $H_2O$ and then with a saturated aqueous sodium chloride solution. After drying over $MgSO_4$ and concentration to dryness, the crude is chromatographed on silica gel, elution being carried out with a 99/1 mixture of dichloromethane and methanol, to give 1.42 g of tert-butyl [(1R)-1-(4-chlorobenzyl)-2-(3-{cyclohexyl[(di-ethylamino)carbonyl]amino}-8-azabicyclo[3.2.1]oct-8-yl)-2-oxoethyl] carbamate.

1.5: N-[8-(4-chloro-D-phenylalanyl)-8-azabicyclo [3.2.1]oct-3-yl]-N-cyclohexyl-N',N'-diethylurea 1.42 g of tert-butyl [(1R)-1-(4-chlorobenzyl)-2-(3-{cyclohexyl[(diethylamino)carbonyl]amino}-8-azabicyclo[3.2.1]

oct-8-yl)-2-oxoethyl]carbamate are placed in 12 ml of 2N hydrochloric acid in diethyl ether. The reaction medium is stirred at ambient temperature for 3 h. 5 ml of 2N hydrochloric acid in diethyl ether are added and stirring is maintained for 16 h. After evaporation to dryness, the crude obtained is chromatographed on silica gel, elution being carried out with a 95/5/0.5 mixture of dichloromethane, methanol and aqueous ammonia. 1.03 g of N-[8-(4-chloro-D-phenylalanyl)-8-azabicyclo[3.2.1]oct-3-yl]-N-cyclohexyl-N',N'-diethylurea are obtained.

1.6: tert-butyl 4-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}piperidine-1-carboxylate 0.41 g of N-[8-(4-chloro-D-phenylalanyl)-8-azabicyclo[3.2.1]oct-3-yl]-N-cyclohexyl-N',N'-diethylurea is dissolved in 4 ml of dichloromethane under $N_2$ in the presence of 0.17 g of N-BOC-piperidone and of 0.23 g of sodium triacetoxyborohydride, and the mixture is stirred at ambient temperature for 16 h. After evaporation and hydrolysis, extraction is carried out with ethyl acetate until the aqueous phase is completely depleted. The organic phase is washed with $H_2O$ and then with a saturated aqueous sodium chloride solution. Drying over $MgSO_4$ and concentration to dryness are carried out. The crude is chromatographed on silica gel, elution being carried out with a 98/2 mixture of dichloromethane and methanol. 0.37 g of tert-butyl 4-{[(1R)-1-(4-chlorobenzyl)-2-(3-{cyclohexyl[(diethylamino)carbonyl]amino}-8-azabicyclo-[3.2.1]oct-8-yl)-2-oxoethyl]amino}piperidine-1-carboxylate is then obtained.

1.7: N-[8-(4-chloro-N-piperidin-4-yl-D-phenylalanyl)-8-azabicyclo [3.2.1]oct-3-yl]-N-cyclohexyl-N',N'-diethylurea hydrochloride 0.37 g of tert-butyl 4-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}-piperidine-1-carboxylate is solubilized in 2.74 ml of 2N hydrochloric acid in diethyl ether. The reaction medium is stirred at ambient temperature for 16 h. After evaporation to dryness, the crude is chromatographed on silica gel, elution being carried out with a 95/5/0.5 mixture of dichloromethane, methanol and aqueous ammonia. 0.27 g of N-[8-(4-chloro-N-piperidin-4-yl-D-phenylalanyl)-8-azabicyclo-[3.2.1]oct-3-yl]-N-cyclohexyl-N',N'-diethylurea hydrochloride is then obtained.

Melting point>210° C., M+H$^+$=572, $[\alpha]_D^{20}$=−2.0 (c=1.002 g/100 ml, MeOH).

EXAMPLE 2

N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea (Compound No. 4)

2.1: N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea 0.30 g of the N-[8-(4-chloro-D-phenylalanyl)-8-azabicyclo[3.2.1]oct-3-yl]-N-cyclohexyl-N',N'-diethylurea endo compound, obtained in step 1.5, is dissolved in 3 ml of dichloromethane under $N_2$ in the presence of 0.061 g of tetrahydro-4H-pyran-4-one and of 0.17 g of sodium triacetoxyborohydride. The reaction medium is stirred at ambient temperature for 3 days. After evaporation and hydrolysis with a saturated aqueous sodium hydrogen carbonate solution, extraction is carried out with ethyl acetate until the aqueous phase is completely depleted. The organic phase is washed with $H_2O$ and then with a saturated aqueous sodium chloride solution. Drying over $MgSO_4$ and concentration to dryness are carried out. The crude is chromatographed on silica gel, elution being carried out with a 99/1 and then 98/2 mixture of dichloromethane and methanol. 0.23 g of N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea is then obtained.

2.2: N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea hydrochloride 0.23 g of N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea is dissolved in 5 ml of diethyl ether and then 0.20 ml of 2N hydrochloric acid in diethyl ether is added. Trituration, rinsing with diethyl ether, and then filter-drying of the precipitate obtained are performed. The crystals are then dried over $P_2O_5$ under reduced pressure. 0.19 g of N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea is obtained.

Melting point>210° C., M+H$^+$=573, $[\alpha]_D^{20}$=−5.9 (c=0.553 g/100 ml, DMSO). $^1$H NMR (200 MHz, DMSO-d+$D_2O$): 7.31 (d, J=8 Hz, 2H), 7.19 (d, J=8 Hz, 2H), 4.62 (m, 1H), 4.41 (m, 1H), 3.90 (m, 3H) 3.25 (m, 5H), 2.88 (m, 5H), 2.10-1.05 (m, 23H), 0.91 (t, J=4 Hz, 6H). Elemental analysis: exp % C=61.46, % H: 8.10, % N: 8.88; th: % 61.50, % H: 8.34, % N: 8.96.

EXAMPLE 3

N-[8-(N-8-azabicyclo[3.2.1]oct-3-yl-4-chloro-D-phenylalanyl)-8-azabicyclo[3.2.1]oct-3-yl]-N-cyclohexyl-N',N'-diethylurea (Compound No. 5)

3.1: tert-butyl 3-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}-8-azabicyclo-[3.2.1]octane-8-carboxylate 0.24 g of the N-[8-(4-chloro-D-phenylalanyl)-8-azabicyclo[3.2.1]oct-3-yl]-N-cyclohexyl-N',N'-diethylurea endo compound, obtained in step 1.5, is dissolved in 5 ml of dichloromethane under $N_2$ in the presence of 0.169 g of Boc-nortropanone and of 0.26 g of sodium triacetoxyborohydride. The reaction medium is stirred at ambient temperature for 16 h. 0.085 g of Boc-nortropinone and 2.6g of sodium triacetoxyborohydride are added and stirring is maintained for 2 days. After evaporation to dryness, 1 ml of methanol and 4 g of Dowex® 50X2 resin are added. The mixture is stirred for 1 h 30 min. After filtration and washing of the resin with tetrahydrofuran and methanol, the expected compound is released by adding a 1N solution of aqueous ammonia in methanol. The methanol is evaporated off, to give 0.21 g of endo and exo tert-butyl 3-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}-8-azabicyclo[3.2.1]octane-8-carboxylate. The subsequent synthesis is carried out on this mixture.

3.2: N-[8-(N-8-azabicyclo[3.2.1]oct-3-yl-4-chloro-D-phenylalanyl)-8-azabicyclo[3.2.1]oct-3-yl]-N-cyclohexyl-N',N'-diethylurea hydrochloride 0.21 g of tert-butyl 3-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}-8-azabicyclo[3.2.1]octane-8-carboxylate is placed in 1.53 ml of 2N hydrochloric acid in diethyl ether. The reaction medium is stirred at ambient temperature overnight. Trituration, rinsing with diethyl ether, and filter-drying of the precipitate obtained are carried out. The crystals are then dried over $P_2O_5$ under reduced pressure. 0.12 g of N-[8-(N-8-azabicyclo[3.2.1]oct-3-yl-4-chloro-D-phenylalanyl)-8-azabicyclo[3.2.1]oct-3-yl]-N-cyclohexyl-N',N'-diethylurea hydrochloride is obtained.

Melting point=155° C.; $M+H^+=598$.

EXAMPLE 4

N-[8-(4-chloro-N-{[(2S,4R)-4-hydroxypyrrolidin-2-yl]methyl}-D-phenylalanyl)-8-azabicyclo[3.2.1]oct-3-yl]-N-cyclohexyl-N',N'-diethylurea
(Compound No. 11)

4.1: tert-butyl (2S,4R)-4-hydroxy-2-{[methoxy(methyl)amino]carbonyl}pyrrolidine-1-carboxylate 1.85 g of (4R)-1-(tert-butoxycarbonyl)-4-hydroxy-L-proline are dissolved in 80 ml of dichloromethane at 0° C. under $N_2$. 3.72 ml of triethylamine and 1.97 ml of tert-butyl chloroformate are added. The reaction medium is stirred at ambient temperature for 1 h. In parallel, a solution of dimethylhydroxylamine is prepared by adding 1.86 ml of triethylamine to a solution of 1.56 g of dimethyl-hydroxylamine hydrochloride in dichloromethane, and then by filtering off the triethylamine hydrochloride. This second solution is added gently, at 0° C., to the first. The reaction medium is stirred at ambient temperature for 16 h. After hydrolysis with a 0.5N aqueous hydrochloric acid solution, extraction is carried out with dichloromethane until the aqueous phase is completely depleted. The organic phase is dried over $MgSO_4$ and concentrated to dryness. 0.9 g of tert-butyl (2S,4R)-4-hydroxy-2-{[methoxy(methyl)amino]-carbonyl}pyrrolidine-1-carboxylate is obtained, which product is subsequently used as it is.

4.2: tert-butyl (2S,4R)-2-formyl-4-hydroxypyrrolidine-1-carboxylate 0.9 g of tert-butyl (2S,4R)-4-hydroxy-2-{[methoxy(methyl)amino]carbonyl}pyrrolidine-1-carboxylate is dissolved in 31 ml of diethyl ether under $N_2$. The reaction medium is placed at 0° C. and 3.41 ml of 1N lithium aluminium hydride in tetrahydrofuran is carefully added. The mixture is stirred at 0° C. for 2 h. After hydrolysis with an aqueous potassium sulphate solution, extraction is carried out with diethyl ether until the aqueous phase is completely depleted. Drying over $MgSO_4$ and concentration to dryness are carried out. The crude obtained is chromatographed on silica gel, elution being carried out with a 9/1 mixture of dichloromethane and methanol. 0.45 g of tert-butyl (2S,4R)-2-formyl-4-hydroxypyrrolidine-1-carboxylate is obtained.

4.3: tert-butyl (2S,4R)-2-({[(1R)-1-(4-chlorobenzyl)-2-(3-{cyclohexyl[(diethylamino)carbonyl]-amino}-8-azabicyclo[3.2.1]oct-8-yl)-2-oxoethyl]amino}-methyl)-4-hydroxypyrrolidine-1-carboxylate 0.24 g of the N-[8-(4-chloro-D-phenylalanyl)-8-azabicyclo[3.2.1]oct-3-yl]-N-cyclohexyl-N',N'-diethylurea endo compound, obtained in step 1.5, is dissolved in 3 ml of dichloromethane under $N_2$ in the presence of 0.16 g of tert-butyl (2S,4R)-2-formyl-4-hydroxypyrrolidine-1-carboxylate and of 0.233 g of sodium triacetoxyborohydride. The reaction medium is stirred at ambient temperature for 16 h. After evaporation to dryness, 1 ml of methanol and 4 g of Dowex® 50X2 resin are added. The mixture is stirred for 1 h 30 min. After filtration and washing of the resin with tetrahydrofuran and methanol, the expected compound is released by adding a 1N solution of aqueous ammonia in methanol. The methanol is evaporated off, to give 0.28 g of tert-butyl (2S,4R)-2-({[(1R)-1-(4-chlorobenzyl)-2-(3-{cyclohexyl[(diethylamino)carbonyl]-amino}-8-azabicyclo[3.2.1]oct-8-yl)-2-oxoethyl]amino}-methyl)-4-hydroxypyrrolidine-1-carboxylate.

4.4: N-[8-(4-chloro-N-{[(2S,4R)-4-hydroxypyrrolidin-2-yl]methyl}-D-phenylalanyl)-8-azabicyclo[3.2.1]oct-3-yl]-N-cyclohexyl-N',N'-diethylurea 0.28 g of tert-butyl (2S,4R)-2-({[(1R)-1-(4-chlorobenzyl)-2-(3-{cyclohexyl[(diethylamino)carbonyl]-amino}-8-azabicyclo[3.2.1]oct-8-yl)-2-oxoethyl]amino}-methyl)-4-hydroxypyrrolidine-1-carboxylate is dissolved in 5 ml of diethyl ether, and then 2.7 ml of 2N hydrochloric acid in diethyl ether are added. Trituration, rinsing with diethyl ether, and filter-drying of the precipitate obtained are carried out, which precipitate is chromatographed on silica gel, elution being carried out with a 90/10/1 mixture of dichloromethane, methanol and aqueous ammonia. 0.18 g of N-[8-(4-chloro-N-{[(2S,4R)-4-hydroxypyrrolidin-2-yl]methyl}-D-phenylalanyl)-8-azabicyclo[3.2.1]oct-3-yl]-N-cyclohexyl-N',N'-diethylurea is obtained.

4.5: N-[8-(4-chloro-N-{[(2S,4R)-4-hydroxypyrrolidin-2-yl]methyl}-D-phenylalanyl)-8-azabicyclo-[3.2.1]oct-3-yl]-N-cyclohexyl-N',N'-diethylurea hydrochloride 0.18 g of N-[8-(4-chloro-N-{[(2S,4R)-4-hydroxypyrrolidin-2-yl]methyl}-D-phenylalanyl)-8-azabicyclo[3.2.1]oct-3-yl]-N-cyclohexyl-N',N'-diethylurea is placed in 0.4 ml of 2N hydrochloric acid in diethyl ether. Trituration, rinsing with diethyl ether, and filter-drying of the precipitate obtained are carried out. 0.16 g of N-[8-(4-chloro-N-{[(2S,4R)-4-hydroxypyrrolidin-2-yl]methyl}-D-phenylalanyl)-8-azabicyclo-[3.2.1]oct-3-yl]-N-cyclohexyl-N',N'-diethylurea hydrochloride is obtained.

Melting point>200° C., $M+H^+=588$, $[\alpha]_D^{20}=-10.70$ (c=0.646 g/100 ml, DMSO).

EXAMPLE 5

N-{8-[N-(2-aminoethyl)-4-chloro-D-phenylalanyl]-8-azabicyclo[3.2.1]oct-3-yl}-N-cyclohexyl-N',N'-diethylurea (Compound No. 18)

5.1: tert-butyl (2-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}ethyl)-carbamate 0.24 g of the N-[8-(4-chloro-D-phenylalanyl)-8-azabicyclo[3.2.1]oct-3-yl]-N-cyclohexyl-N',N'-diethylurea endo compound, obtained in step 1.5, is dissolved in 5 ml of dichloromethane under $N_2$ in the presence of 0.10 g of tert-butyl N-(2-oxoethyl)carbamate and of 0.22 g of sodium triacetoxyborohydride. The reaction medium is stirred at ambient temperature for 16 h. After evaporation to dryness, 0.05 g of tert-butyl N-(2-oxoethyl)carbamate and 0.1 g of sodium triacetoxyborohydride are added, and stirring is maintained for 3 days. After the addition of 1 ml of methanol and 4 g of Dowex® 50X2 resin, the mixture is stirred for 1 h 30 min. After filtration and washing of the resin with tetrahydrofuran and methanol, the expected compound is released by adding a 1N solution of aqueous ammonia in methanol. The methanol is evaporated off, to give 0.14 g of tert-butyl (2-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}ethyl)carbamate.

5.2: N-{8-[N-(2-aminoethyl)-4-chloro-D-phenylalanyl]-8-azabicyclo[3.2.1]oct-3-yl}-N-cyclohexyl-N',N'-diethylurea 0.14 g of tert-butyl (2-{[(1R)-1-(4-chlorobenzyl)-2-(3-{cyclohexyl[(diethylamino)carbonyl]amino}-8-azabicyclo[3.2.1]oct-8-yl)-2-oxoethyl]amino}ethyl)-carbamate is placed in 1.1 ml of 2N hydrochloric acid in diethyl ether. The reaction medium is stirred at ambient temperature for 1 h. Trituration, rinsing with diethyl ether and filter-drying of the precipitate obtained are carried out. The salt thus obtained is chromatographed on silica gel, elution being carried out with a 98/2/0.2 and then 95/5/0.5 mixture of dichloromethane, methanol and aqueous ammonia. 0.05 g of N-{8-[N-(2-aminoethyl)-4-chloro-D-phenylalanyl]-8-azabicyclo[3.2.1]oct-3-yl}-N-cyclohexyl-N',N'-diethylurea hydrochloride is obtained.

Melting point=105° C., M+H$^+$=532, $[\alpha]_D^{20}$=−12.60 (c=0.521 g/100 ml, DMSO).

EXAMPLE 6

N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea (Compound No. 22)

6.1: tert-butyl (3R)-3-{[methoxy(methyl)-amino]carbonyl}-3,4-dihydroisoquinoline-2(1H)-carboxylate 6.95 g of Boc-D-Tic-OH are dissolved in 25 ml of dichloromethane. 2.69 g of dimethylhydroxylamine hydrochloride and 11.68 g of bromotrispyrrolidino-phosphonium hexafluorophosphate are added. After cooling of the solution to 0° C., 9.72 ml of diisopropylamine are slowly added. The reaction medium is then stirred at ambient temperature for 16 h. After hydrolysis, extraction is carried out with ethyl acetate until the aqueous phase is completely depleted. Drying over $MgSO_4$ and concentration to dryness are carried out. The crude obtained is chromatographed on silica gel, elution being carried out with a 99/1 mixture of dichloromethane and methanol. 7.4 g of tert-butyl (3R)-3-{[methoxy(methyl)amino]carbonyl}-3,4-dihydroisoquinoline-2(1H)-carboxylate are obtained.

6.2: tert-butyl (3R)-3-formyl-3,4-dihydroisoquinoline-2(1H)-carboxylate 7.4 g of tert-butyl (3R)-3-{[methoxy(methyl)-amino]carbonyl}-3,4-dihydroisoquinoline-2(1H)-carboxylate are dissolved in 31 ml of diethyl ether under $N_2$. The reaction medium is placed at 0° C. and 0.98 g of lithium aluminium hydride is carefully added. The mixture is stirred at 0° C. for 45 min. After hydrolysis with an aqueous potassium sulphate solution, extraction is carried out with diethyl ether until the aqueous phase is completely depleted. The organic phases are washed with a 3N aqueous hydrochloric acid solution, with a saturated aqueous sodium hydrogen carbonate solution, then with $H_2O$, and finally with a saturated aqueous sodium chloride solution. Drying over $MgSO_4$ and concentration to dryness are carried out. 3.5 g of tert-butyl (3R)-3-formyl-3,4-dihydroisoquinoline-2(1H)-carboxylate are obtained, which product is subsequently used as it is.

6.3: tert-butyl (3R)-3-({[(1R)-1-(4-chlorobenzyl)-2-methoxy-2-oxoethyl]amino}methyl)-3,4-dihydroisoquinoline-2(1H)-carboxylate 3.5 g of tert-butyl (3R)-3-formyl-3,4-dihydroisoquinoline-2(1H)-carboxylate are dissolved in 67 ml of dichloromethane under $N_2$ in the presence of 4.02 g of D-4-chlorophenyl alanine methyl ester and of 3.69 g of sodium triacetoxyborohydride. The reaction medium is stirred at ambient temperature for 16 h. After hydrolysis, extraction is carried out with dichloromethane until the aqueous phase is completely depleted. Drying over $MgSO_4$ and concentration to dryness are carried out. The crude is chromatographed on silica gel, elution being carried out with a gradient of methanol in dichloromethane ranging from 1% to 3%. 6.1 g of tert-butyl (3R)-3-({[(1R)-1-(4-chlorobenzyl)-2-methoxy-2-oxoethyl]amino}methyl)-3,4-dihydroisoquinoline-2(1H)-carboxylate are then obtained.

6.4: N-{[(3R)-2-(tert-butoxycarbonyl)-1,2,3,4-tetrahydroisoquinolin-3-yl]methyl}-4-chloro-D-phenylalanine 6.4 g of tert-butyl (3R)-3-({[(1R)-1-(4-chlorobenzyl)-2-methoxy-2-oxoethyl]amino}methyl)-3,4-dihydroisoquinoline-2(1H)-carboxylate are dissolved in 150 ml of a mixture of tetrahydrofuran/water/MeoH (1/1/1) at 0° C., and 0.99 g of lithium hydroxide hydrate is added. Stirring is maintained at 0° C. for 3 h. 0.5 g of lithium hydroxide hydrate is then added. The medium is maintained at 0° C. for 16 h. Potassium sulphate is added up to a pH of 7. The precipitate obtained is filter-dried and rinsed with diethyl ether. After drying over $P_2O_5$, 7.2 g of N-{[(3R)-2-(tert-butoxycarbonyl)-1,2,3,4-tetrahydroisoquinolin-3-yl]methyl}-4-chloro-D-phenylalanine are obtained.

6.5: tert-butyl (3R)-3-({[(1R)-1-(4-chlorobenzyl)-2-(3-{cyclohexyl[(diethylamino)carbonyl]amino}-8-azabicyclo[3.2.1]oct-8-yl)-2-oxoethyl]amino}methyl)-3,4-dihydroisoquinoline-2(1H)-carboxylate 0.2 g of N-8-azabicyclo[3.2.1]oct-3-yl-N-cyclohexyl-N',N'-diethylurea endo compound, obtained in step 1.3, is dissolved in 3.25 ml of dichloromethane in the presence of 0.35 g of N-{[(3R)-2-(tert-butoxycarbonyl)-1,2,3,4-tetrahydroisoquinolin-3-yl]methyl}-4-chloro-D-phenylalanine, obtained in step 6.5, of 0.088 g of hydroxybenzotriazole, of 0.125 g of 1-(3-di-methylaminopropyl)-3-ethylcarbodiimide hydrochloride and of 0.17 ml of diisopropylethylamine. The mixture is stirred at ambient temperature for 16 h. After evaporation to dryness, the residue is hydrolysed and extracted with ethyl acetate until the aqueous phase is completely depleted. After drying over $MgSO_4$ and concentration to dryness, the crude is chromatographed on silica gel, elution being carried out with a gradient of methanol in dichloromethane ranging from 0% to 3%. 0.29 g of tert-butyl (3R)-3-({[(1R)-1-(4-chlorobenzyl)-2-(3-{cyclohexyl[(diethylamino)carbonyl]amino}-8-azabicyclo[3.2.1]oct-8-yl)-2-oxoethyl]amino}methyl)-3,4-dihydroisoquinoline-2(1H)-carboxylate is obtained.

6.6: N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea 0.29 g of tert-butyl (3R)-3-({[(1R)-1-(4-chlorobenzyl)-2-(3-{cyclohexyl[(diethylamino)carbonyl]-amino}-8-azabicyclo[3.2.1]oct-8-yl)-2-oxoethyl]amino}-methyl)-3,4-dihydroisoquinoline-2(1H)-carboxylate is placed in 1.1 ml of 4N hydrochloric acid in dioxane. The reaction medium is stirred at ambient temperature for 1 h. After hydrolysis with a 1N aqueous sodium hydroxide solution, extraction is carried out with dichloromethane until the aqueous phase is completely depleted. Drying over $MgSO_4$ and concentration to dryness are carried out. The crude obtained is chromatographed on silica gel, elution being carried out with a 98/2 mixture of dichloromethane and methanol. 0.12 g of N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea is obtained.

6.7: N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea hydrochloride 0.12 g of N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea is dissolved in 5 ml of dichloromethane and 0.4 ml of 4N hydrochloric acid in dioxane is added. After evaporation, the residue is taken up in diethyl ether, rinsing is carried out with diethyl ether and the precipitate obtained is filter-dried. 0.12 g of N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea hydrochloride is obtained.

Melting point=182° C., M+H$^+$=634, $[\alpha]_D^{20}$=–10.20 (c=0.857 g/100 ml, DMSO).

EXAMPLE 7

N-{8-[4-chloro-N-(pyridin-2-yl-methyl)-D-phenylalanyl]-8-azabicyclo[3.2.1]oct-3-yl}-N-cyclohexyl-N',N'-diethylurea (Compound No. 23)

7.1: N-{8-[4-chloro-N-(pyridin-2-ylmethyl)-D-phenylalanyl]-8-azabicyclo[3.2.1]oct-3-yl}-N-cyclohexyl-N',N'-diethylurea 0.24 g of N-[8-(4-chloro-D-phenylalanyl)-8-azabicyclo[3.2.1]oct-3-yl]-N-cyclohexyl-N',N'-diethylurea, obtained in step 1.5, is dissolved in 3 ml of dichloromethane under $N_2$ in the presence of 0.05 ml of 2-pyridinecarboxaldehyde and of 0.22 g of sodium triacetoxyborohydride. The reaction medium is stirred at ambient temperature for 16 h. After evaporation to dryness and addition of 1 ml of methanol and 4 g of Dowex® 50X2 resin, the mixture is stirred for 1 h 30 min. After filtration and washing of the resin with tetrahydrofuran and methanol, the expected compound is released by adding a 1N solution of aqueous ammonia in methanol. The methanol is evaporated off, to give 0.054 g of N-{8-[4-chloro-N-(pyridin-2-ylmethyl)-D-phenylalanyl]-8-azabicyclo[3.2.1]oct-3-yl}-N-cyclohexyl-N',N'-diethylurea.

7.2: N-{8-[4-chloro-N-(pyridin-2-ylmethyl)-D-phenylalanyl]-8-azabicyclo[3.2.1]oct-3-yl}-N-cyclohexyl-N',N'-diethylurea hydrochloride 0.054 g of is placed in 2 ml of isopropanol and 0.06 ml of 2N hydrochloric acid in diethyl ether is added. After evaporation, the residue is taken up in diethyl ether, rinsing is carried out with diethyl ether and the precipitate obtained is filter-dried. 0.045 g of N-{8-[4-chloro-N-(pyridin-2-ylmethyl)-D-phenylalanyl]-8-azabicyclo[3.2.1]oct-3-yl}-N-cyclohexyl-N',N'-diethylurea hydrochloride is obtained.

Melting point=119° C., M+H$^+$=580.

The table that follows illustrates the chemical structures and the physical properties of some examples of compounds according to the invention, i.e. of the compounds of formula (Ia), corresponding to compounds of formula (I) in which $R_a=R_{a'}=R_5=$H and $R_3$ represents a chlorine atom located in the para-position on the phenyl ring to which it is attached. In this table:
   in the "salt" column, "HCl" represents a compound in the form of a hydrochloride,
   "Mp" represents the melting point measured for the compound,
   Me and Et represent, respectively, methyl and ethyl groups.

TABLE
(Ia)
| No. | R₁ | R₂ | R₄ | Salt | Mp (°C.) |
|---|---|---|---|---|---|
| 1 | cyclohexyl | —CON(Et)₂ | 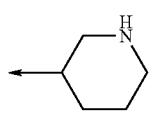 | HCl | >210 |
| 2 | cyclohexyl | —CON(Et)₂ | 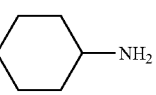 | HCl | 162 |
| 3 | cyclohexyl | —CON(Et)₂ |  | HCl | 208 |
| 4 | cyclohexyl | —CON(Et)₂ | 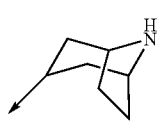 | HCl | >210 |
| 5 | cyclohexyl | —CON(Et)₂ | 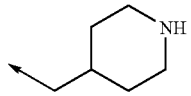 | HCl | 155 |
| 6 | cyclohexyl | —CON(Et)₂ | 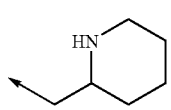 | HCl | 171 |
| 7 | cyclohoexyl | —CON(Et)₂ | 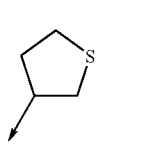 | HCl | 166 |
| 8 | cyclohoexyl | —CON(Et)₂ | 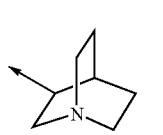 | HCl | >200 |
| 9 | cyclohoexyl | —CON(Et)₂ | 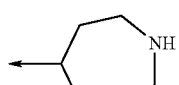 | HCl | 192 |
| 10 | cyclohoexyl | —CON(Et)₂ | 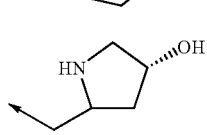 | HCl | 159 |
| 11 | cyclohoexyl | —CON(Et)₂ |  | HCl | >200 |

TABLE-continued

*Structure (Ia): bicyclic amine with R1, R2 substituents on one nitrogen, connected via C(=O) to a chiral center bearing NHR4 and a 4-chlorobenzyl group.*

| No. | R₁ | R₂ | R₄ | Salt | Mp (° C.) |
|---|---|---|---|---|---|
| 12 | cyclohoexyl | —CO—N(Et)₂ | (3-hydroxy-pyrrolidin-5-yl)methyl | CF₃CO₂H | 90 |
| 13 | cyclohoexyl | —CO—N(Et)₂ | (3-hydroxy-pyrrolidin-5-yl)methyl | HCl | |
| 14 | cyclohoexyl | —CO—N(Et)₂ | (1-phenylpiperidin-4-yl)methyl | HCl | 152 |
| 15 | cyclohoexyl | —CO—N(Et)₂ | (1-benzylpyrrolidin-3-yl)methyl | HCl | 162 |
| 16 | cyclohoexyl | —CO—N(Et)₂ | (pyrrolidin-3-yl)methyl | HCl | 220 |
| 17 | cyclohoexyl | —CO—N(Et)₂ | [4-(4-hydroxyphenyl)cyclohexyl]methyl | HCl | 176 |
| 18 | cyclohoexyl | —CO—N(Et)₂ | —CH₂CH₂NH₂ | HCl | 105 |
| 19 | cyclohoexyl | —CO—N(Et)₂ | —(CH₂)₃NH₂ | HCl | 215 |
| 20 | cyclohoexyl | —CO—N(Et)₂ | —CH(Me)CH=N—OH | HCl | 132 |
| 21 | cyclohoexyl | —CO—N(Et)₂ | —CH(Me)CH₂F | HCl | >200 |
| 22 | cyclohoexyl | —CO—N(Et)₂ | (1,2,3,4-tetrahydroisoquinolin-3-yl)methyl | HCl | 182 |
| 23 | cyclohoexyl | —CO—N(Et)₂ | (pyridin-2-yl)methyl | HCl | 119 |

TABLE-continued

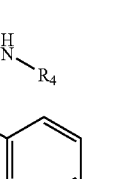

(Ia)

| No. | R₁ | R₂ | R₄ | Salt | Mp (° C.) |
|---|---|---|---|---|---|
| 24 | cyclohoexyl | —CO—N(Et)₂ |  | HCl | >200 |
| 25 | cyclohoexyl | —CO—N(Et)₂ | | HCl | |
| 26 | cyclohoexyl | —CO—N(Et)₂ | | HCl | |
| 27 | cyclohoexyl | —CO—N(Et)₂ |  | HCl | 170 |
| 28 | cyclohoexyl | —CO—N(Et)₂ | 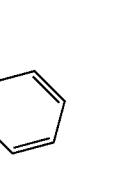 | HCl | 158 |

The compounds according to the invention were the subject of pharmacological assays to determine their melanocortin receptor agonist effect, in particular their MC3 and/or MC4 receptor agonist effect.

Evaluation of the Affinity of the Compounds of Formula (I) According to the Invention with Respect to MC3 and MC4 Receptors This affinity assay is carried out by measuring the binding of [$^{125}$I]-[Nle$^4$-D-Phe$^7$]-☐-MSH to cell membranes. The displacement of this radioligand is used to identify inhibitors of the specific binding to recombinant melanocortin receptors.

For this assay, membranes prepared from CHO-K1 cells expressing the human MC4 receptor at high density (Euroscreen) or membranes, that were purchased (Perkin Elmer Life Sciences, Receptor Biology), of HEK-293 cells expressing hMC3 receptors were used. CHO-K1 cells transfected with the hMC4 receptor gene (Euroscreen) are seeded into DMEM/Nutrient Mix F12 culture medium containing 10% foetal calf serum (Biowhittaker), 1% sodium pyruvate, 1% L-glutamine, 1% non-essential amino acids, 0.4 mg/ml geneticin (G418) and 0.5% PenStrep, these products being provided by Gibco/BR1, except the calf serum. At 80% confluency, the cells are scraped off and the cell pellets are frozen at −80° C.

A tube of cells (approximately 70×10⁶ cells) is thawed on ice and resuspended in 10 ml of binding buffer [25 mM HEPES, pH 7.0, 1 mM MgCl₂, 1.5 mM CaCl₂, 100 mM NaCl, 1 mM 1,10-phenanthroline and 1 tablet of Complete$^{TR}$ (protease inhibitor from Roche) in 50 ml of buffer] using a polytron for 20 seconds. The suspension is centrifuged for 20 min at 19 500 rpm at 4° C. The supernatant is discarded and the pellet is resuspended in 5 ml of binding buffer. The amount of proteins present in the sample is assayed using a Bradford test, and the concentration is adjusted to 3 μg/25 μl by dilution in binding buffer. [$^{125}$I]-[Nle$^4$, D-Phe$^7$]-☐-MSH is diluted in binding buffer+0.2% BSA. SPA beads (wheatgerm agglutinin polyvinyltoluene, Amersham Pharmacia Biotech) are hydrated in the binding buffer+0.2% BSA and are then mixed with the cell homogenate so as to obtain 3 μg of cell proteins and 250 μg of beads in 50 μl. The products to be tested (diluted in 10% DMSO), in an amount of 10 μl at a concentration of 10 times the final concentration, are distributed into a clear-bottomed 96-well white plate (CORNING 3604 Polystyrene Non-Binding Surface). The nonspecific binding is defined by NDP-☐MSH at 10⁻⁷ M. The total binding is measured by the number of counts per minute in the presence of the radioligand alone. The distribution of the membranes-beads suspension (50 μl/well) is followed by distribution of the solution of [$^{125}$I]-[Nle$^4$, D-Phe$^7$]-☐-MSH, 40 μl/well (final concentration of 100 pM), for a final volume of 100 μl/well. After incubation at ambient temperature for 6 h, counting is carried out in a Microbeta TriLux scintillation counter. The $IC_{50}$ value for the compounds corresponds to the concentration that displaces the specific binding of the radioligand by 50%.

It is thus determined that the compounds according to the invention exhibit affinity for MC3 and/or MC4 receptors. Their $IC_{50}$ values with respect to MC3 and MC4 receptors are less than 10 µM, and for most of them between 1 nM and 1 µM. As an example, compound No. 3 of the table exhibits an $IC_{50}$ of 280 nM with respect to the MC4 receptor.

Evaluation of the Agonist Activity of the Compounds of Formula (I) According to the Invention, With Respect to MC3 and MC4 Receptors A functional assay is used to differentiate between the agonist activity and the antagonist activity. For this, the formation of cyclic adenosine monophosphate (cAMP) generated by activation of the MC3 receptor or of the MC4 receptor is assayed.

CHO-K1 cells, expressing the human MC4 receptor at a moderate density (Euroscreen), are seeded into DMEM/Nutrient Mix F12 culture medium (Gibco/BR1) containing 10% of foetal calf serum, 0.5% sodium pyruvate, 1% L-glutamine, 1% non-essential amino acids, 200 mg/l hygromycin B and 0.5% PenStrep, these products being provided by Gibco/BR1, except the calf serum (Biowhittaker) and hygromycin B (Sigma).

CHO(dhfr-) cells expressing the human MC3 receptor are seeded into MEM Eagle culture medium (Sigma) containing 10% of dialysed calf serum, 1% L-glutamine, 1% sodium pyruvate, 20 mg/500 ml L-proline, 0.3 mg/ml Geneticin and 0.5% PenStrep, these products being provided by Gibco/BRI, except for the dialysed calf serum (Cambrex) and the L-proline (Sigma).

The compounds to be tested (diluted in 10% DMSO), in an amount of 10 µl at a concentration of 10 times the final concentration, are added to the plates of cells (final volume=100 µl/well). After incubation for 1 hour (37° C., 5% $CO_2$), the amount of cAMP is assayed using Tropix kits (Appelera) according to the supplier's documentation. The intrinsic activity of the compounds is calculated by comparing the stimulation of cAMP by these compounds to the stimulation induced by 30 nM of NDP☐MSH (maximum of 100%). The $EC_{50}$ value for the compounds corresponds to the concentration which produces 50% of the maximum stimulation obtained with this compound.

It is thus determined that the compounds according to the invention are MC3- and/or MC4-receptor agonists. They have $EC_{50}$ values with respect to MC3 and MC4 receptors of less than 10 µM, and for most of them of between 1 nM and 1 µM. As examples, compound No. 3 of the table has an $EC_{50}$ of 330 nM with respect to the MC3 receptor, and of 28 nM with respect to the MC4 receptor.

As the compounds according to the invention exhibit melanocortin receptor agonist activity, they can therefore be used in the manufacture of medicaments. Thus, according to another of its aspects, a subject of the invention is medicaments which comprise a compound of formula (I), or an addition salt of the latter with a pharmaceutically acceptable acid, or else a hydrate or a solvate of the compound of formula (I).

These medicaments find their use in therapeutics, in pathologies in which melanocortin receptors, in particular MC3 and/or MC4 receptors, are involved: this involves in particular the treatment and prevention of obesity, diabetes and sexual dysfunctions that can affect both sexes, such as erectile dysfunctions, cardiovascular diseases such as myocardial infarction or hypertension, and also in anti-inflammatory uses or in the treatment of alcohol dependency.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, or a hydrate or a solvate of said compound, and also at least one pharmaceutically acceptable excipient.

Said excipients are chosen, according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its possible salt, solvate or hydrate, can be administered in unit administration form, as a mixture with conventional pharmaceutical excipients, to animals and to human beings for the prophylaxis or the treatment of the conditions or of the diseases above.

Suitable unit administration forms comprise oral forms such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

A preferred administration form is oral administration.

By way of example, a unit administration form of a compound according to the invention in the form of a tablet can comprise the following constituents:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

There may be specific cases where higher or lower dosages are appropriate; such dosages do not depart from the context of the invention. According to the usual practice, the dosage appropriate for each patient is determined by the physician according to the method of administration, and the weight and response of said patient.

According to another of its aspects, the present invention also relates to a method of treating the pathologies indicated above, which comprises the administration, to a patient, of an effective dose of a compound according to the invention, or one of its pharmaceutically acceptable salts or hydrates or solvates.

The invention claimed is:

1. A compound corresponding to formula (I):

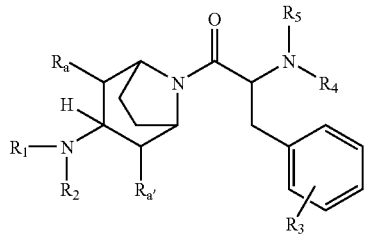

(I)

in which:

R$_a$ and R$_{a'}$, which may be identical to or different from one another, represent a hydrogen atom, or an alkyl or cycloalkyl group, R$_1$ represents a hydrogen atom, or an alkyl, cycloalkyl, heterocycloalkyl or aryl group, R$_2$ represents a group of formula —(CH$_2$)$_x$—(CO)$_y$—Y or —(CO)$_y$—(CH$_2$)$_x$—Y, in which:
x=0, 1, 2, 3 or 4,
y=0 or 1,
Y represents a hydrogen atom, or a hydroxyl, alkyl, cycloalkyl, alkoxy, aryl, heteroaryl or —NR$_{11}$R$_{12}$ group, Y being different from a hydrogen atom when x=y=0, R$_{11}$ and R$_{12}$ which may be identical to or different from one another, represent a hydrogen atom, or an alkyl, cycloalkyl, alkoxy or —NR$_{13}$R$_{14}$ group, or else R$_{11}$ and R$_{12}$ form, together with the nitrogen atom to which they are attached, a mono- or bicyclic structure containing from 4 to 10 ring members and optionally comprising 1 to 3 additional hetero atoms and/or 1 to 3 ethylenic or acetylenic unsaturations, this ring being optionally substituted in any of the positions with 1 to 3 groups chosen from halogen atoms, and hydroxyl, alkyl, cycloalkyl and alkoxy groups, R$_{13}$ and R$_{14}$, which may be identical to or different from one another, represent a hydrogen atom, or an alkyl, cycloalkyl or alkoxy group, or else R$_{13}$ and R$_{14}$ form, together with a nitrogen atom to which they are attached, a mono- or bicyclic structure as defined above, R$_3$ represents 1 to 3 groups, which may be identical to or different from one another, located in any positions of the ring to which they are attached and chosen from halogen atoms, and alkyl, cycloalkyl, —OR, —NRR', —CO—NRR', —NR—CO—R', —NR—CO—NRR', —NR—COOR', —NO$_2$, —CN and —COOR groups, R$_5$ represents a hydrogen atom or an alkyl, R$_4$ is chosen from:
(1) a group of formula (a), (b) or (c) optionally substituted with an oxo group:

(a)

-continued

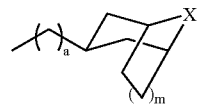

(b)

(c)

in which each of the rings of formulae (a), (b) and (c) may be substituted, in any position, with 1 to 4 groups R$_7$, which may be identical to or different from one another, and in which:
a=0, 1, 2 or 3,
p=0, 1, 2 or 3,
m=0, 1 or 2, X represents an oxygen or sulphur atom, or a ring member —C(R$_6$)(R$_7$)— or —N(R$_{10}$)—, wherein R$_6$ is chosen from:
a hydrogen atom, a halogen atom,
a group —(CH$_2$)$_x$—OR$_8$, —(CH$_2$)$_x$—COOR$_8$, —(CH$_2$)$_x$—NR$_8$R$_9$, —(CH$_2$)$_x$—CO—NR$_8$R$_9$ or —(CH$_2$)$_x$—NR$_8$—COR$_9$, in which x=0, 1, 2, 3 or 4,
an alkyl, cycloalkyl, heterocycloalkyl, aryl, heteroaryl, alkylaryl, alkylheteroaryl, —CO-alkyl, —CO-cycloalkyl, —CO-heterocycloalkyl, —CO-aryl, —CO-heteroaryl, —CO-alkylaryl, —CO-alkylheteroaryl, —CS-alkyl, —CS-cycloalkyl, —CS-heterocycloalkyl, —CS-aryl, —CS-heteroaryl, —CS-alkylaryl, —CS-alkylheteroaryl, —CS—NR$_8$R$_9$ or —C(=NH)—NR$_8$R$_9$ group,
a fused or nonfused cycloalkyl or heterocycloalkyl group located in the spiro position on the ring of formula (a) to which it is attached,
a cycloalkyl or heterocycloalkyl group fused with an aryl or heteroaryl group, R$_7$ is chosen from hydrogen and halogen atoms, and alkyl, cycloalkyl, aryl, heteroaryl, alkylaryl, alkylheteroaryl, —OR, —O-aryl, —O-heteroaryl, —O-alkylaryl, —O-alkylheteroaryl, —NRR', —CO—NRR', —NR—CO—R', —NR—CO—NRR', —NR—COOR', —NO$_2$, —CN and —COOR groups, R$_8$ and R$_9$ are chosen, independently of one another, from a hydrogen atom, and alkyl, cycloalkyl, heterocycloalkyl, aryl, heteroaryl, alkylaryl, alkylheteroaryl, —CO-alkyl, —CO-cycloalkyl, —CO-hetero-cycloalkyl, —CO-aryl, —CO-heteroaryl, —CO-alkylaryl, —CO-alkylheteroaryl, —SO$_2$-alkyl, —SO$_2$-cycloalkyl, —SO$_2$-heterocycloalkyl, —SO$_2$-aryl, —SO$_2$-heteroaryl, —SO$_2$-alkylaryl, —SO$_2$-alkylheteroaryl, —C(=NH)—NRR', —COOR, —CO—NRR', —CS—NRR' and —(CH$_2$)$_x$—OR groups, where x=0, 1, 2, 3 or 4;

or else R$_8$ and R$_9$ together form a cycloalkyl or a heterocycloalkyl;

R$_{10}$ is chosen from:
a hydrogen atom,
a group —(CH$_2$)$_x$—OR$_8$, —(CH$_2$)$_x$—COOR$_8$, —(CH$_2$)$_x$—NR$_8$R$_9$, —(CH$_2$)$_x$—CO—NR$_8$R$_9$, —(CH$_2$)$_x$—NR$_8$—COR$_9$ or —(CH$_2$)$_x$—COR$_8$, in which x=0, 1, 2, 3 or 4, a cycloalkyl or heterocycloalkyl group fused with an aryl or heteroaryl group, an alkyl, cycloalkyl, heterocycloalkyl, aryl, heteroaryl, alkylaryl, alkylheteroaryl, —CO-alkyl, —CO-cycloalkyl, —CO-heterocycloalkyl, —CO-aryl, —CO-heteroaryl, —CO-alkylaryl, —CO-alkylheteroaryl, —CS-alkyl, —CS-cycloalkyl, —CS-heterocycloalkyl, —CS-aryl, —CS-heteroaryl, —CS-alkylaryl, —CS-alkylheteroaryl, —CS—NR$_8$R$_9$, —C(=NH)—NR$_8$R$_9$, —SO$_2$-alkyl, —SO$_2$-cycloalkyl, —SO$_2$-heterocycloalkyl, —SO$_2$-aryl, —SO$_2$-heteroaryl, —SO$_2$-alkylaryl, —SO$_2$-alkylheteroaryl or —SO$_2$—NR$_8$R$_9$ group, or else R$_{10}$ forms, with the nitrogen atom to which it is attached and a carbon atom located in any position of the cyclic structure of formula (a), but not adjacent to said nitrogen atom, a bridge comprising from 3 to 5 members, R and R' represent, independently of one another, a hydrogen atom, or an alkyl, cycloalkyl, heterocycloalkyl, aryl, heteroaryl, alkylaryl or alkylheteroaryl group, wherein the alkyl, cycloalkyl, heterocycloalkyl, aryl and heteroaryl groups being optionally substituted with one or more groups chosen from the groups R, R', —OR, —NRR', —CO—NRR', —NR—CO—R', —NR—CO—NRR', —NO$_2$, —CN and —COOR, OCOR, COR, OCONRR', NRCOOR', (2) a group of formula -A-R$_{18}$, -A-CH=N—R$_{19}$, -A-N(R$_{20}$)-A'-R$_{19}$, -A-CO—N(R$_{20}$)-A'-R$_{19}$, -A-CH(NH$_2$)—R$_{19}$ or -A-N(R$_{20}$)—COO-A', in which A and A' represent a linear or branched alkyl group, R$_{18}$ represents a halogen atom, or an —NH$_2$, hydroxyl or phenyl group, R$_{19}$ represents a hydrogen atom, or a hydroxyl, phenyl, benzyl or heteroaryl group, and R$_{20}$ represents a hydrogen atom or a benzyl group, (3) a group of formula (d):

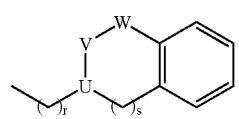

(d)

optionally substituted, in any positions, with 1 to 4 groups R$_7$, which may be identical to or different from one another, as defined above, and in which r is equal to 1, 2 or 3, s is equal to 0 or 1, and one of U, V or W represents a nitrogen atom, the others among U, V and W representing methylene ring members, or (4) a —(CH$_2$)$_r$-heteroaryl group, where r is equal to 1, 2 or 3, in the form of a base or of an addition salt with an acid.

2. The compound of claim 1, wherein R$_1$ represents a cycloalkyl group, in the form of a base or of an addition salt with an acid.

3. The compound of claim 1, wherein

R$_2$ is chosen from the following groups: —CO—R$_{15}$, —CO—NR$_{16}$R$_{17}$, —CO—NR$_{15}$—NR$_{16}$R$_{17}$, —CO-aryl, —CO-heteroaryl, —CO—(CH$_2$)$_x$—NR$_{16}$R$_{17}$, —(CH$_2$)$_x$—NR$_{16}$R$_{17}$, —(CH$_2$)$_x$—OH, —(CH$_2$)$_x$-aryl, —(CH$_2$)$_x$-heteroaryl, —(CH$_2$)$_x$—CO—R$_{15}$ and —(CH$_2$)$_x$—CO—NR$_{16}$R$_{17}$, in which:

x=0, 1, 2, 3 or 4 and x'=1, 2, 3 or 4,

R$_{15}$ represents a hydrogen atom, or an alkyl, cycloalkyl or alkoxy group, and R$_{16}$ and R$_{17}$, which may be identical to or different from one another, represent a hydrogen atom, or an alkyl, cycloalkyl or alkoxy group, or else R$_{16}$ and R$_{17}$ form, together with the nitrogen atom to which they are attached, a mono- or bicyclic structure containing from 4 to 10 ring members and optionally comprising 1 to 3 additional hetero atoms and/or 1 to 3 ethylenic or acetylenic unsaturations, this ring being optionally substituted in any positions with 1 to 3 groups chosen from halogen atoms, and hydroxyl, alkyl, cycloalkyl and alkoxy groups, in the form of a base or of an addition salt with an acid.

4. The compound of claim 1, wherein R$_2$ represents a group —CO—NR$_{16}$R$_{17}$, where R$_{16}$ and R$_{17}$ represent alkyl or alkoxy groups, in the form of a base or of an addition salt with an acid.

5. The compound of claim 1, wherein R$_3$ represents 1 to 3 groups, which may be identical to or different from one another, chosen from halogen atoms, in the form of a base or of an addition salt with an acid.

6. The compound of claim 1, wherein R$_4$ is chosen from:

(1) a group of formula (a-5), (a-6) or (b-2) below:

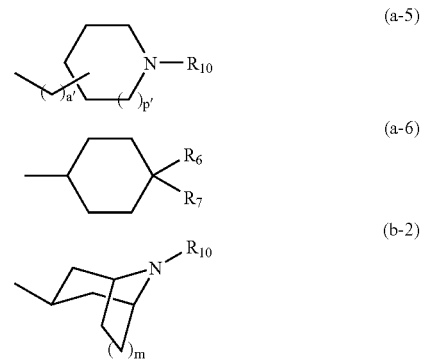

in which each of the rings of formulae (a-5), (a-6) and (b-2) can be substituted, in any positions, with 1 to 4 groups R$_7$, which may be identical to or different from one another, as defined in claim 1, and in which a'=0 or 1, p'=0 or 1, and R$_6$, R$_7$ and R$_{10}$ are as defined in claim 1, (2) a group of formula -A-R$_{18}$ or -A-CH=N—R$_{19}$, where A, R$_{18}$ and R$_{19}$ are as defined in claim 1, (3) a group of formula (d-1), where r=1, 2 or 3:

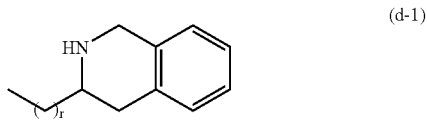

(d-1)

(4) a group —(CH$_2$)$_r$-furyl or —(CH$_2$)$_r$-pyridinyl, where r is equal to 1, 2 or 3, in the form of a base or of an addition salt with an acid.

7. The compound of claim 1, wherein R$_5$ represents a hydrogen atom, in the form of a base or of an addition salt with an acid.

8. The compound of claim 1, wherein R$_a$=R$_{a'}$=H, in the form of a base or of an addition salt with an acid.

9. The method for preparing a compound of claim 1, wherein a reductive amination of a compound of formula (V):

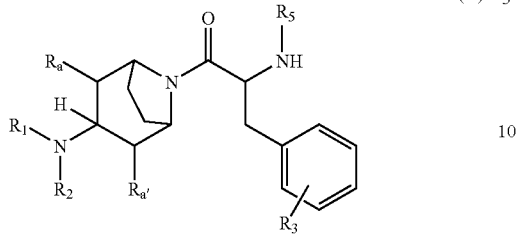

is carried out in the presence of a derivative of the group $R_a$ of ketone type, $R_1$, $R_2$, $R_3$, $R_4$, $R_5$, $R_a$ and $R_{a'}$ being as defined in any one of claims 1 to 8.

10. A compound of formulae (IV) and (V), in which $R_1$, $R_2$, $R_3$, $R_5$, $R_a$ and $R_{a'}$ are as defined in claim 1 and Pg represents a protective group:

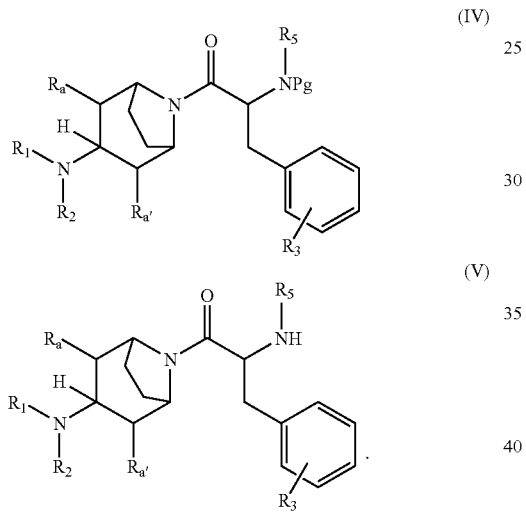

11. A pharmaceutical composition, which comprises a compound of claim 1, or an addition salt of this compound with a pharmaceutically acceptable acid, in combination with at least one pharmaceutically acceptable excipient.

12. A pharmaceutical composition, which comprises a compound of claim 8, or a pharmaceutically acceptable salt thereof, in combination with at least one pharmaceutically acceptable excipient.

13. A method of effecting agonistic activity of melanocortin receptor so as to alleviate a condition selected from obesity, diabetes and erectile dysfunctions that can affect both sexes, or in the treatment of alcohol dependency comprising administering to a patient in need thereof an effective amount of a compound of claim 1.

14. The method of claim 13, wherein said sexual dysfunctions consist of erectile dysfunctions.

15. A compound selected from the group consisting of:
1: N-[8-(4-chloro-N-piperidin-4-yl-D-phenylalanyl)-8-azabicyclo[3.2.1]oct-3-yl]-N-cyclohexyl-N',N'-diethylurea
2: N-[8-(4-chloro-N-piperidin-3-yl-D-phenylalanyl)-8-azabicyclo[3.2.1]oct-3-yl]-N-cyclohexyl-N',N'-diethylurea
3: N-{8-[N-(4-aminocyclohexyl)-4-chloro-D-phenylalanyl]-8-azabicyclo[3.2.1]oct-3-yl}-N-cyclohexyl-N',N'-diethylurea
4: N-{8-[4-chloro-N-(tetrahydro-2H-pyran-4-yl)-D-phenylalanyl]-8-azabicyclo[3.2.1]oct-3-yl}-N-cyclohexyl-N',N'-diethylurea
5: N-[8-(N-8-azabicyclo[3.2.1]oct-3-yl-4-chloro-D-phenylalanyl)-8-azabicyclo[3.2.1]oct-3-yl]-N-cyclohexyl-N',N'-diethylurea
6: N-{8-[4-chloro-N-(piperidin-4-ylmethyl)-D-phenylalanyl]-8-azabicyclo[3.2.1]oct-3-yl}-N-cyclohexyl-N',N'-diethylurea
7: N-{8-[4-chloro-N-(piperidin-2-ylmethyl)-D-phenylalanyl]-8-azabicyclo[3.2.1]oct-3-yl}-N-cyclohexyl-N',N'-diethylurea
8: N-{8-[4-chloro-N-(tetrahydro-3-thienyl)-D-phenylalanyl]-8-azabicyclo[3.2.1]oct-3-yl}-N-cyclohexyl-N',N'-diethylurea
9: N-[8-(N-1-azabicyclo[2.2.2]oct-3-yl-4-chloro-D-phenylalanyl)-8-azabicyclo[3.2.1]oct-3-yl]-N-cyclohexyl-N',N'-diethylurea
10: N-[8-(N-azepan-4-yl-4-chloro-D-phenylalanyl)-8-azabicyclo[3.2.1]oct-3-yl]-N-cyclohexyl-N',N'-diethylurea
11: N-[8-(4-chloro-N-{[(2S,4R)-4-hydroxypyrrolidin-2-yl]methyl}-D-phenylalanyl)-8-azabicyclo[3.2.1]oct-3-yl]-N-cyclohexyl-N',N'-diethylurea
12: N-[8-(4-chloro-N-{[(2R,4R)-4-hydroxypyrrolidin-2-yl]methyl}-D-phenylalanyl)-8-azabicyclo[3.2.1]oct-3-yl]-N-cyclohexyl-N',N'-diethylurea
13: N-[8-(4-chloro-N-{[(2R,4S)-4-hydroxypyrrolidin-2-yl]methyl}-D-phenylalanyl)-8-azabicyclo[3.2.1]oct-3-yl]-N-cyclohexyl-N',N'-diethylurea
14: N-{8-[4-chloro-N-(1-phenylpiperidin-4-yl)-D-phenylalanyl]-8-azabicyclo[3.2.1]oct-3-yl}-N-cyclohexyl-N',N'-diethylurea
15: N-(8-{N-[(1-benzylpyrrolidin-3-yl)-methyl]-4-chloro-D-phenylalanyl}-8-azabicyclo-[3.2.1]oct-3-yl)-N-cyclohexyl-N',N'-diethylurea
16: N-[8-(4-chloro-N-pyrrolidin-3-yl-D-phenylalanyl)-8-azabicyclo[3.2.1]oct-3-yl]-N-cyclohexyl-N',N'-diethylurea
17: N-(8-{4-chloro-N-[4-(4-hydroxyphenyl)-cyclohexyl]-D-phenylalanyl}-8-azabicyclo[3.2.1]oct-3-yl)-N-cyclohexyl-N',N'-diethylurea
18: N-{8-[N-(2-aminoethyl)-4-chloro-D-phenyl-alanyl]-8-azabicyclo[3.2.1]oct-3-yl}-N-cyclohexyl-N',N'-diethylurea
19: N-{8-[N-(3-aminopropyl)-4-chloro-D-phenylalanyl]-8-azabicyclo[3.2.1]oct-3-yl}-N-cyclo-hexyl-N',N'-diethylurea
20: N-(8-{4-chloro-N-[(2E)-2-(hydroxyimino)-1-methylethyl]-D-phenylalanyl}-8-azabicyclo[3.2.1]oct-3-yl)-N-cyclohexyl-N',N'-diethylurea
21: N-{8-[4-chloro-N-(2-fluoro-1-methylethyl)-D-phenylalanyl]-8-azabicyclo[3.2.1]oct-3-yl}-N-cyclohexyl-N',N'-diethylurea
22: N-(8-{4-chloro-N-[(3R)-1,2,3,4-tetrahydroisoquinolin-3-ylmethyl]-D-phenylalanyl}-8-azabicyclo[3.2.1]oct-3-yl)-N-cyclohexyl-N',N'-diethylurea
23: N-{8-[4-chloro-N-(pyridin-2-ylmethyl)-D-phenylalanyl]-8-azabicyclo[3.2.1]oct-3-yl}-N-cyclohexyl-N',N'-diethylurea 24: N-{8-[4-chloro-N-(2-furylmethyl)-D-phenylalanyl]-8-azabicyclo[3.2.1]oct-3-yl}-N-cyclohexyl-N',N'-diethylurea 25: N-(8-{4-chloro-N-[(2R)-pyrrolidin-2-yl-methyl]-D-phenylalanyl}-8-azabicyclo[3.2.1]oct-3-yl)-N-cyclohexyl-N',N'-diethylurea 26: N-(8-{4-chloro-N-[(2S)-pyrrolidin-2-ylmethyl]-D-phenylalanyl}-8-azabicyclo[3.2.1]oct-3-yl)-N-cyclohexyl-N',N'-diethylurea 27: N-[8-(N-azetidin-3-yl-4-chloro-D-phenylalanyl)-8-azabicyclo[3.2.1]oct-3-yl]-N-cyclohexyl-N',N'-diethylurea 28: N-(8-{N-[(1-benzylpyrrolidin-3-yl)-methyl]-4-chloro-D-phenylalanyl}-8-azabicyclo[3.2.1]-oct-3-yl)-N-cyclohexyl-N',N'-diethylurea.

\* \* \* \* \*

UNITED STATES PATENT AND TRADEMARK OFFICE
CERTIFICATE OF CORRECTION

PATENT NO. : 7,569,582 B2  Page 1 of 1
APPLICATION NO. : 11/626973
DATED : August 4, 2009
INVENTOR(S) : Alain Braun et al.

It is certified that error appears in the above-identified patent and that said Letters Patent is hereby corrected as shown below:

In column 7, line 17, delete "—$(CH_2)_x$—CO—$R_{15}$" and insert -- –$(CH_2)_x$, –CO–$R_{15}$ --, therefor.

In column 7, line 17, delete "—$(CH_2)_x$—CO—$NR_{16}R_{17}$," and insert -- –$(CH_2)_x$, –CO–$NR_{16}R_{17}$, --, therefor.

In column 11, line 53, delete "3-yl)" and insert -- 3-yl} --, therefor.

In column 12, line 6, delete "N-([(2S,4R)" and insert -- N-{[(2S,4R) --, therefor.

In column 12, line 9, delete "N-([{2R,4R)" and insert -- N-{[(2R,4R) --, therefor.

In column 12, line 34, delete "N-{[8" and insert -- N-{8 --, therefor.

In column 47, line 1, in Claim 9, delete "The" and insert -- A --, therefor.

In column 47, line 19, in Claim 10, delete "formulae (IV) and (V)," and insert
-- formula (IV) or (V), --, therefor.

In column 49, line 4, in Claim 15, delete "2-yl-methyl]" and insert -- 2-ylmethyl] --, therefor.

Signed and Sealed this
First Day of May, 2012

David J. Kappos
*Director of the United States Patent and Trademark Office*